United States Patent [19]

Chene et al.

[11] Patent Number: 4,690,708
[45] Date of Patent: Sep. 1, 1987

[54] HERBICIDES DERIVED FROM ARYLOXYBENZENECARBOXYLIC ACID IMIDES

[75] Inventors: Alain Chene; Guy Borrod, both of Lyons, France

[73] Assignee: Rhone-Poulenc Agrochimie, Lyons, France

[21] Appl. No.: 629,895

[22] Filed: Jul. 11, 1984

[30] Foreign Application Priority Data

Jul. 12, 1983 [FR] France ................ 83 11858

[51] Int. Cl.⁴ .......................... A01N 43/40
[52] U.S. Cl. ........................ 71/94; 546/24; 546/241; 546/244; 546/272; 546/287; 546/288; 546/293; 546/296; 546/297; 546/300; 558/1; 558/3; 558/6; 558/7; 558/9; 558/48 CG; 564/74
[58] Field of Search ............ 71/94; 546/24, 241, 546/244, 272, 287, 288, 293, 296, 297; 260/453.1, 453.7; 564/74

[56] References Cited

U.S. PATENT DOCUMENTS

| | | | |
|---|---|---|---|
| 3,772,370 | 11/1973 | Surrey ................ | 260/570.5 |
| 3,957,852 | 5/1976 | Fujikawa et al. ........... | 260/473 R |
| 3,979,437 | 9/1976 | Theissen ................ | 260/471 R |
| 4,039,588 | 8/1977 | Wilson et al. ........... | 260/613 R |
| 4,070,178 | 1/1978 | Johnson et al. .............. | 71/105 |
| 4,093,446 | 6/1978 | Bayer et al. ............... | 71/109 |
| 4,209,318 | 6/1980 | Johnson ..................... | 71/88 |
| 4,231,962 | 11/1980 | Reinehr et al. ........... | 564/272 |
| 4,263,227 | 4/1981 | Krass ..................... | 564/256 |
| 4,285,723 | 8/1981 | Cartwright et al. ........ | 71/103 |
| 4,344,789 | 8/1982 | Krass ..................... | 71/105 |
| 4,401,602 | 8/1983 | Krass ..................... | 260/465 E |
| 4,419,123 | 12/1983 | Swithenbank ............ | 71/98 |

FOREIGN PATENT DOCUMENTS

| | | |
|---|---|---|
| 23890 | 11/1981 | European Pat. Off. . |
| 23891 | 11/1981 | European Pat. Off. . |
| 2434571 | 3/1980 | France . |
| 72/105858 | 6/1974 | Japan . |
| 1377677 | 12/1974 | United Kingdom . |
| 2049695A | 12/1980 | United Kingdom . |
| 2068949A | 8/1981 | United Kingdom . |
| 2103610 | 2/1983 | United Kingdom . |

OTHER PUBLICATIONS

Von H. E. Kunzel et al., 130 *Die Makromolekulaire Chemic,* pp. Title, Index, 102–111 and 134–135.

*Primary Examiner*—Joseph L. Schofer
*Assistant Examiner*—Bernard Lipman
*Attorney, Agent, or Firm*—Morgan & Finnegan

[57] ABSTRACT

A herbicide of the formula:

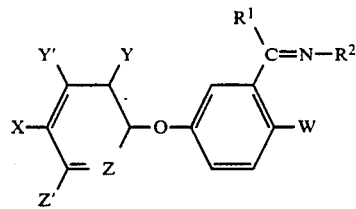

in which:

Z is N or CX',
W, Y, Y', X, Z' and X' represent H, a halogen atom, $NO_2$, CN or a polyhalogenoalkyl, alkyl or alkoxy group,
$R^2$ represents H, halogen, substituted alkyl, allyl, propargyl, CN, $NR^4R^5$, $C(X^2)R^7$, $C(X^2)X^3R^8$, $C(X^2)NR^4R^5$, $SO_2F$, $SO_2OR^8$, $SO_2NR^4R^5$ or $P(X^2)R^9R^{10}$,
$R^1$ is halogen, $X^2R^3$ or $NR^4R^5$,
$R^3$ is optionally substituted alkyl or is allyl or propargyl,
$R^4$, $R^7$ and $R^8$ represent H, alkyl, cycloalkyl, phenyl, allyl, propargyl or the like,
$R^5$ represents $R^4$, a cation or $OR^6$, $R^6$ being H, a cation or alkyl,
$X^2$ and $X^3$ are O or S,
$R^9$ and $R^{10}$ are H, alkyl, OH, OM or $R^1$, and
M is a cation.

3 Claims, No Drawings

HERBICIDES DERIVED FROM ARYLOXYBENZENECARBOXYLIC ACID IMIDES

The invention relates to herbicidal compounds of the aryloxybenzenecarbonimide type.

5-[2'-Chloro-4'-(trifluoromethyl)phenoxy]-2-nitrobenzoic acid, also called acifluorfen, and its salts are known, as is their herbicidal activity.

In particular, it has been proposed to apply acifluorfen and its salts to soya crops in a post-emergence treatment in order to control weeds, especially dicotyledons. In an application of this type, the properties required of a herbicide, at the dose in question, are:

the capacity to control the major weeds or target weeds, and the selectivity with respect to soya.

In attempts to improve the herbicidal properties of acifluorfen and its salts, a large number of derivatives of these compounds have been proposed, in particular the alkyl, cycloalkyl, thioalkyl and phenyl esters, as well as the monoalkylamides or dialkylamides. Compounds of these types are described in U.S. Pat. Nos. 3,652,645, 3,784,635, 3,873,302, 3,983,168, 3,907,866, 3,798,276, 3,928,416, 4,063,929 and so on. European Pat. Nos. 3,416 and 23,392 describe sulphonamides derived from phenoxybenzoic acids. It is known in this field that the herbicidal properties are not predictable (European Pat. Nos. 21,692 and 27,387 and so on).

One object of the invention is to provide products offering a good combination of herbicidal properties as regards the activity on weeds and the selectivity on crops. Another object of the invention is to provide products having a good selectivity for crops other than soya, especially cereals, cotton and rice.

The invention thus relates to products of the formula:

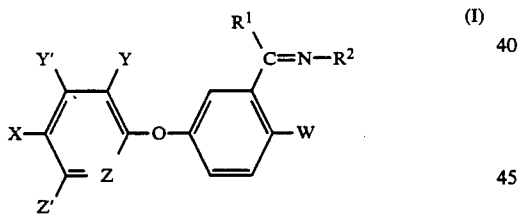

in which:

Z represents the nitrogen atom or a group —C(X')=,

W, Y, Y', X, Z' and X' represent the hydrogen atom, a halogen atom, a group $NO_2$ or CN, a polyhalogenoalkyl group such as $CF_3$, or an alkyl or alkoxy group, the various alkyl or alkoxy groups mentioned above having most frequently from 1 to 4 carbon atoms, $R^1$ represents a halogen atom or a group $X^2R^3$ or $NR^4R^5$, $R^2$ represents the hydrogen atom, a halogen atom, a substituted alkyl group, an allyl or propargyl group, a group CN, a group $NR^4R^5$, a group $C(X^2)R^7$, a group $C(X^2)X^3R^8$ or $C(X^2)NR^4R^5$, a group $SO_2F$, $SO_2OR^8$ or $SO_2NR^4R^5$ or a group $P(X^2)R^9R^{10}$, $R^3$ represents an alkyl group, which may be optionally substituted by, for example, one or more halogen, alkoxy ($C_1$-$C_4$) or alkylthio ($C_1$-$C_2$) groups or any other of the substituents mentioned in connection with $R_2$ below, or an allyl or propargyl group, $R^4$ represents the hydrogen atom, an alkyl, cycloalkyl or phenyl group, each group being optionally substituted, an allyl or propargyl group or an alkylcarbonyl or alkylsulphonyl group, $R^5$ has one of the meanings given for $R^4$ or represents a cation or a group $OR^6$, $R^6$ being the hydrogen atom, a cation or an optionally substituted alkyl group, $X^2$ and $X^3$ represent the oxygen or sulphur atom, $R^7$ represents the hydrogen atom, an alkyl, cycloalkyl or phenyl group, this group being optionally substituted, or an alkenyl or alkynyl group, $R^8$ represents a cation or has one of the meanings given for $R^7$, and $R^9$ and $R^{10}$, which are identical or different, represent the hydrogen atom, an optionally substituted alkyl group, a hydroxyl group or a group OM, M representing a cation, or have one of the meanings given for $R^1$, with the proviso that (a) $R^2$ is not $COOCH_3$ when $R^1$ is $OCH_3$, W is $NO_2$, Y' and Z' are H and X is $CF_3$, Y is Cl and Z is —CH=, and with the further proviso that (b) $R^2$ is not H when X is $NO_2$.

More specifically, these radicals are most frequently chosen so that:

W represents the hydrogen atom, a halogen atom, in particular Cl, Br or F, or a group $NO_2$ or CN;

Y represents the hydrogen atom, a halogen atom, in particular Cl, Br or F, or a group $NO_2$, CN, $CF_3$ or $CH_3$;

Y', Z' and X' represent the hydrogen atom or a halogen atom, in particular Cl, Br or F;

X represents a halogen atom, in particular Cl, Br or F, or a group $NO_2$, $CF_3$, $CH_2$ or $C_2H_5$;

$R^1$ represents a halogen atom, preferably chlorine, or a group $X^2R^3$ or $NR^4R^5$;

$R^2$ represents:

the hydrogen atom, or a halogen atom, in particular Cl or F;

an alkyl group, having most frequently from 1 to 4 carbon atoms, substituted by:
one or more halogen atoms, in particular Cl, Br or F,
one or more alkoxy or alkylthio groups having most frequently from 1 to 4 carbon atoms,
one or more groups $NO_2$ or CN,
a phenyl group, itself optionally substituted, in particular, by one or more halogen atoms, or
a carbonyl group or one of its derivatives of the salt, ester or amide type, in particular a group $COOR^8$, an allyl or propargyl group,
a group CN,
a group $NR^4R^5$,
a group $C(X^2)R^7$,
a group $C(X^2)X^3R^8$,
a group $C(X^2)NR^4R^5$,
a group $SO_2F$,
a group $SO_2OR^8$,
a group $SO_2NR^4R^5$, or
a group $P(X^2)R^9R^{10}$;

$R^3$ represents:

an alkyl group, having most frequently from 1 to 4 carbon atoms, optionally substituted by:
one or more halogen atoms, in particular Cl, Br or F,
one or more alkoxy or alkylthio groups having most frequently from 1 to 4 carbon atoms,
one or more groups $NO_2$ or CN, a phenyl group, itself optionally substituted, in particular, by one or more halogen atoms,
a carboxyl group or one of its derivatives of the salt, ester or amide type, in particular a group $COOR^8$, or
an alkylcarbonyl group, in particular acetyl, or
an allyl or propargyl group;

$R^4$ represents:
the hydrogen atom,
an alkyl group having most frequently from 1 to 4 carbon atoms, or a cycloalkyl group having from 3 to 7 carbon atoms in the ring, these alkyl or cycloalkyl radicals being optionally substituted by:
one or more halogen atoms, in particular Cl, Br or F, or
one or more alkoxy or alkylthio groups having most frequently from 1 to 4 carbon atoms,
a phenyl group, itself optionally substituted, in particular, by one or more halogen atoms,
an allyl or propargyl group, or
an alkylcarbonyl or alkylsulphonyl group, in particular acetyl or methanesulphonyl;

$R^5$ has one of the meanings given for $R^4$ or represents an alkali metal cation or ammonium cation or a group $OR^6$, $R^6$ being:
the hydrogen atom,
an alkali metal cation or ammonium cation, or
an alkyl group most frequently having from 1 to 4 carbon atoms, optionally substituted by a carboxyl group or one of its derivatives of the salt, ester or amide type, in particular a group $COOR^8$;

$R^4$ and $R^5$ can optionally together form a single divalent alkylene radical having most frequently from 2 to 5 carbon atoms;

$X^2$ and $X^3$ represent the oxygen or sulphur atom;

$R^7$ represents:
the hydrogen atom,
an alkyl group having most frequently from 1 to 12 carbon atoms and preferably from 1 to 6 carbon atoms, or a cycloalkyl group having 3 to 7 carbon atoms in the ring, these alkyl or cycloalkyl radicals being optionally substituted by:
one or more halogen atoms, in particular Cl, Br or F,
one or more alkoxy or alkylthio groups having most frequently from 1 to 4 carbon atoms,
a phenyl group, itself optionally substituted, in particular, by one or more halogen atoms, or
a carboxyl group or one of its derivatives of the salt, ester or amide type, in particular a group $COOR^8$,
a phenyl group, itself optionally substituted, in particular, by one or more halogen atoms, nitro groups or alkyl radicals having most frequently from 1 to 4 carbon atoms, or
an alkenyl or alkynyl group having most frequently from 2 to 4 carbon atoms, in particular a vinyl, ethynyl, allyl or propargyl radical;

$R^8$ represents a metal cation or ammonium cation or has one of the meanings given for $R^7$; and $R^9$ and $R^{10}$, which are identical or different, have one of the meanings given for $R^1$ or represent:
the hydrogen atom,
an alkyl group optionally substituted by one or more halogen atoms, in particular Cl, Br or F, or
a hydroxyl group or a group OM, M representing a metal cation or ammonium cation.

Unless otherwise stated, the number of carbons in each of the carbon chain moieties or groups aforesaid, e.g. in the alkyl, alkoxy, alkenyl, etc., groups, is preferably from 1 to 4.

A preferred sub-family according to the invention consists of the products of the formula (I) in which L is N or —C(X')=, W is $NO_2$ or Cl, Y is Cl, Y' and Z' are H, X is Cl or $CF_3$ and X' is Cl or F or, preferably, H. Also of particular value are the compounds in which $R^1$ is an alkoxy or thioalkoxy group and also the compounds in which $R^2$ is the hydrogen atom, a substituted alkyl group, an allyl group or a group $C(O)R^7$, $C(O)OR^8$ or

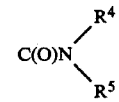

while $R^3$ and $R^8$ are an alkyl radical, $R^4$, $R^5$ and $R^6$ are the hydrogen atom or an alkyl radical, $R^7$ is an alkyl or alkenyl radical and $R^9$ and $R^{10}$ are an alkyl or alkoxy group.

Although the formula (I) given above must be understood as defining the products forming the subject of the invention, these products can exhibit two diastereoisomeric forms E and Z (which may or may not be separable by the chemical techniques known in the art) resulting from the spatial arrangement of the substituents relative to the double bond C=N of the molecule, as shown by the following formulae:

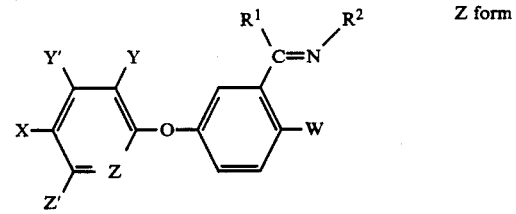

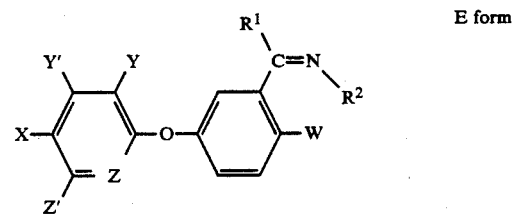

Furthermore, some products can exhibit tautomeric forms, more especially those in the formula of which $R^1$ is a group $NR^4R^5$ where $R^4$ represents the hydrogen atom, as shown by the following scheme:

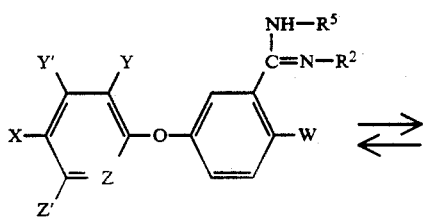

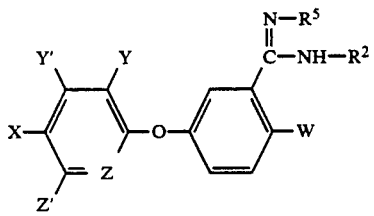

These diastereoisomeric and tautomeric forms are included in the invention for the same reason as the physically distinct forms which result e.g. from differences in conformation, from intramolecular or intermolecular hydrogen bonds or from other analogous phenomena.

The invention also relates to processes for the preparation of the products described above.

In one of these processes, a compound of the formula:

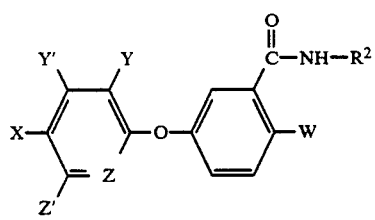

($R^2$ having the meaning given above, except for hydrogen and halogen) is reacted with a halogenating agent so as to give an imidoyl halide of the formula:

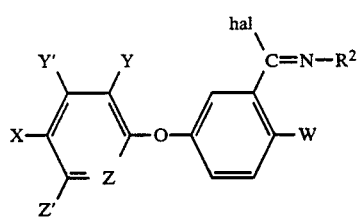

hal representing a halogen atom, preferably chlorine.

Halogenating agents which may be mentioned are $COCl_2$, $SO_2Cl_2$, $(COCl)_2$, $PCl_5$, $PCl_3$, $POCl_3$, $SOCl_2$, and the like; $COCl_2$ and $PCl_5$ are preferred. The reaction is advantageously carried out at between $-30°$ and $+150°$ C. in a solvent, preferably an aliphatic or aromatic hydrocarbon each of which can be optionally substituted with one or more halogens such as methylene chloride, 1,2-dichloroethane, toluene or chlorobenzene, in the presence or absence of an acid acceptor such as a tertiary amine (e.g. triethylamine or pyridine).

The imidoyl halide of the formula (III) is then reacted with a compound of the formula:

$R^1$—H    (IV)

($R^1$ having the meaning given above, excluding the halogen member) so as to produce the compound of the formula (I). The reaction is usually carried out at between 0° and 150° C. in an inert solvent and in the presence of an acid acceptor such as a tertiary amine (e.g. triethylamine or pyridine). Solvents which may be mentioned are optionally halogenated aliphatic or aromatic hydrocarbons each of which can be optionally substituted by one or more halogens, such as methylene chloride, 1,2-dichloroethane or toluere, ethers or nitriles.

In the case where $R^1$ is $OR^3$, some compounds of the formula (I) can also be prepared according to the reaction:

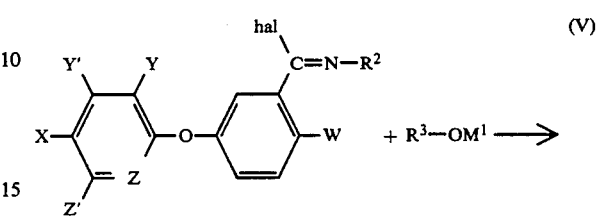

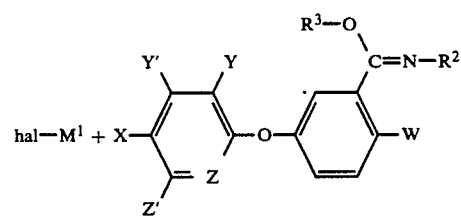

$M^1$ representing the hydrogen atom or an alkali metal atom such as sodium or potassium.

The latter reaction is advantageously carried out at between 10° and 150° C.; it can also be carried out in a solvent consisting of a compound of the formula $R^3OH$. In the case where $R^1$ is $SR^3$ or $NR^4R^5$, some compounds of the formula (I) can also be prepared according to the previous reaction, the reactant of the structure $R^3$—$OM^1$ being replaced, however, with a reactant of the structure:

$R^3$—$SM^1$ or $R^4R^5N$—$M^1$.

These last two reactions are advantageously carried out at between 10° and 150° C. in an inert solvent such as an optionally halogenated aliphatic or aromatic hydrocarbon, each of which can be optionally substituted with one or more halogens, such as toluene, xylene or chlorobenzene.

Some of the compounds of the formula (II) have been prepared. In general, the compounds of the formula (II) can be prepared by reacting the corresponding acid halide with a product of the formula $R^2$—$NH_2$.

In another of these processes, a compound of the formula

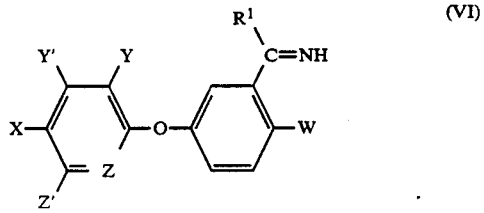

or one of its salts of the formula:

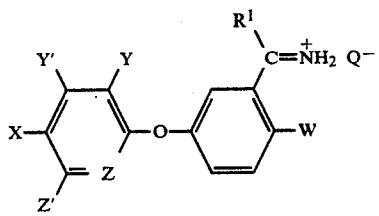

(Q representing a halide anion, in particular chloride, bromide or iodide, a tetrafluoroborate anion or various other anions derived from proton acids, in particular strong acids and $R^1$ having the meaning given above, excluding the halogen member) is reacted with a compound of the formula:

hal representing a halogen atom and $R^2$ having the meaning given above, excluding the hydrogen, halogen and $NR^4R^5$ members.

The reaction is usually carried out at between $-10°$ and $120°$ C. in an inert solvent and in the presence either of an organic acid acceptor such as a tertiary amine (e.g. triethylamine or pyridine) or of a mineral acid acceptor such as an alkali metal hydroxide or magnesium hydroxide. In the case where the acid acceptor is a tertiary amine, solvents which may be mentioned are optionally halogenated aliphatic or aromatic hydrocarbons, each of which may be optionally substituted by one or more halogens, ethers, esters or nitriles. In the case where the acid acceptor is an alkali metal hydroxide or magnesium hydroxide, the reaction can be carried out in a two-phase system, this system comprising an organic phase consisting of an optionally halogenated aliphatic or aromatic hydrocarbon each of which may be optionally substituted by one or more halogens, an ether or an ester, and an aqueous phase.

In the case where $R^2$ is a group $C(X^2)NHR^5$, some compounds of the formula (I) can also be prepared according to the reaction:

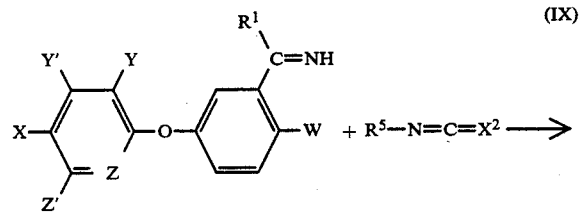

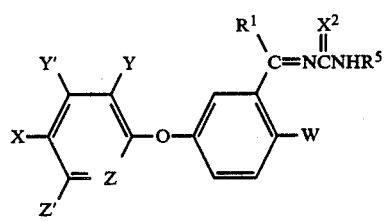

$R^1$ having the meaning given above, excluding the halogen member.

The latter reaction is advantageously carried out at between $10°$ and $150°$ C. in an inert solvent such as an optionally halogenated aliphatic or aromatic hydrocarbon as aforesaid, an ether or a nitrile, and in the presence or absence of a catalyst. Catalysts which may be mentioned without implying a limitation are:

tertiary amines such as triethylamine, pyridine, N,N-dimethylaniline and N,N-diethylaniline, or 1,4-diazabicyclo(2,2,2)octane, or tin derivatives, in particular alkyltin salts such as dibutyltin diacetate or dibutyltin dilaurate.

The isocyanates and isothiocyanates ($R^5-N=C=X^2$) are prepared by processes known per se.

In the case where $R^2$ is a group $C(X^2)NR^4R^5$ or $C(X^2)X^3R^8$, some compounds of the formula (I) can also be prepared by reacting a compound of the formula (VI) ($R^1$ having the meaning given above, excluding the halogen member) with a compound of the formula:

so as to give, in situ, an intermediate of the formula:

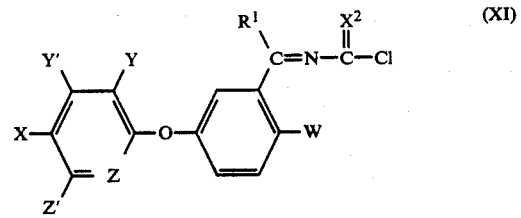

which is generally not isolated from the reaction medium.

The reaction is advantageously carried out at between $-30°$ and $+30°$ C. in a solvent, preferably an optionally halogenated aliphatic or aromatic hydrocarbon as aforesaid, such as methylene chloride, 1,2-dichloroethane, toluene or chlorobenzene, in the presence of an acid acceptor such as:

the compound of the formula (VI) itself, in which case two molar equivalents of this compound are required per molar equivalent of compound of the formula (X), or a tertiary amine (e.g. 2,6-lutidine or 2,4,6-collidine).

The intermediate of the formula (XI) is then reacted with a compound of the formula:

or

so as to produce the compound of the formula (I). The reaction is usually carried out at between $-30°$ and $+30°$ C. in an inert solvent and in the presence of an acid acceptor such as:

a tertiary amine (e.g. triethylamine or pyridine), or the compound of the formula (XII) itself if $R^2$ is a group $C(X^2)NR^4R^5$, in which case two molar equivalents of this compound are required per molar equivalent of compound of the formula (XI).

The solvent is generally the same as the one in which the compound of the formula (XI) was prepared.

In the case where $R^1$ is a group $OR^3$ and $R^2$ is a halogen, some compounds of the formula (I) can also be prepared by reacting a compound of the formula (VI) or one of its salts of the formula (VII) with a halogenating agent such as sodium hypochlorite, t-butyl hypochlorite, sodium hypobromite, bromine, iodine or the like. The reaction is advantageously carried out at between −30° and +30° C. in aqueous media.

Likewise, the compounds of the formula (VI) or their salts of the formula (VII) are obtained by means of methods known per se (see, in particular: S. PATAI, "The Chemistry of Amidines and Imidates", 1975, Interscience publication, JOHN WILEY & SONS, among other references).

In the case where e.g. $R^1$ is a group $OR^3$, $R^3$ representing an alkyl group, some salts of alkyl benzimidates, of the formula:

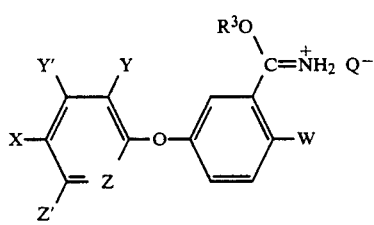
(XIV)

(a having the meaning given above) can be synthesised by O-alkylation of the corresponding benzamides of the formula:

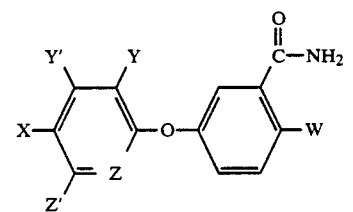
(XV)

with the aid of an alkylating agent such as a dialkyl sulphate, a trialkyloxonium salt, an alkyl fluorosulphonate or the like.

The reaction is usually carried out at between 0° and 120° C. in an inert solvent such as an optionally halogenated aliphatic or aromatic hydrocarbon like methylene chloride, 1,2-dichloroethane or toluene.

The alkyl benzimidates of the formula:

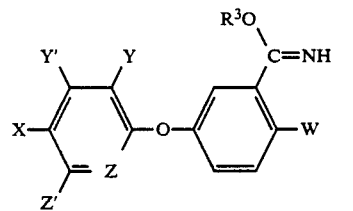
(XVI)

can then be freed from their salts (XIV) by processes known per se, e.g. by reaction with an organic base such as a tertiary amine or an inorganic base such as an alkali metal hydroxide or carbonate, in an organic solvent medium, most often simply at ambient temperature.

Likewise, in the case where $R^1$ is a group $SR^3$, $R^3$ representing an alkyl group, some compounds of formula (VI) or their salts of the formula (VII) can also be prepared according to the previous reaction, the benzamides of the formula (XV) being replaced, however, with the thiobenzamides of the formula:

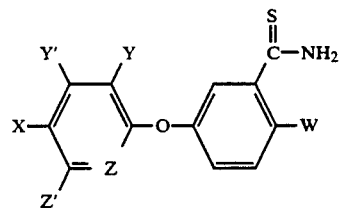
(XVII)

The thiobenzamides of the formula (XVII) are obtained by means of methods known per se (see, in particular: S. PATAI and J. ZABXCKY, "The chemistry of amides", 1970, Interscience Publishers, JOHN WILEY & SONS, among other references).

They can be synthesised e.g. by thionation of the corresponding benzamides of the formula (XV) with the aid of thionating reagents such as $P_4S_{10}$ or

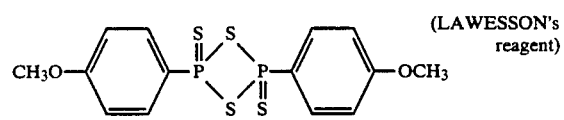
(LAWESSON's reagent)

or the like. The reaction is advantageously carried out at between +60° and +180° C. in a solvent, preferably pyridine or an optionally halogenated aliphatic or aromatic hydrocarbon as aforesaid, such as toluene, xylene or chlorobenzene.

The examples which follow, which are given without implying a limitation, illustrate the invention and show how it can be put into effect.

All the structures of the chemical products were verified by NMR spectrography (nuclear magnetic resonance), IR (infrared), MS (mass spectrography) and microanalysis.

The various analytical techniques used showed that:

firstly, under the conditions of analysis, the products of the formula (I) exist in one or other of the two diastereoisomeric forms E or Z, or as a mixture of the two where either the proportions of each form are equivalent or the proportion of one of the 2 diastereoisomeric forms is preponderant; and secondly, under the conditions of analysis, the products in the formula of which $R^1$ is a group $NHR^5$ (according to the formula (I)) exist in the two tautomeric forms where either the proportions of each form are equivalent or the proportion of one of the 2 tautomeric forms is preponderant.

Examples 1 to 49 illustrate the synthesis and the physical properties of compounds according to the invention.

The different compounds obtained in the various Examples 1 to 38 and 41 to 47 (a compound has the number of the example corresponding thereto) have the formula:

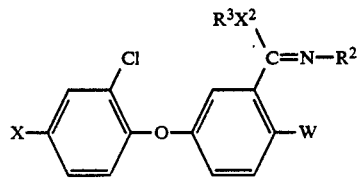

The meanings of the substituents X, W, $X^2R^3$ and $R^2$ for the different compounds, and also the yield of the example and the m.p. (or certain spectral characteristics), are collated in Table (I).

The compounds which have an asymmetric carbon exist in the two enantiomeric forms R or S. In this case, the formula given above must of course be understood as defining one or other of these two forms or as defining a mixture of the two where either the proportions are equivalent (racemate) or the proportion of one or other of them is preponderant.

In the Table (I), the letters IR indicate that the figures shown are infrared absorption bands in $cm^{-1}$; the letters NMR indicate that the figures shown are chemical shifts measured in deuterated chloroform in the presence of tetramethylsilane as the reference.

Example 50 illustrates the application of the products according to the invention in a pre-emergence treatment.

Example 51 illustrates the application of products according to the invention in a post-emergence treatment.

In these application examples, the crops and weeds used were those indicated in Table (II) and the results of Examples 50 and 51 are shown in Table (III).

EXAMPLE 1

This example illustrates the preparation of compound No. 1.

5-[2'-Chloro-4'-(trifluoromethyl)phenoxy]-2-nitro-N-(2-chloroethyl)benzamide (2.3 g; 0.0054 mol) and $PCl_5$ (1.4 g; 0.0067 mol) are suspended in toluene (30 cc).

The mixture is heated to the boil under reflux, with stirring, and the heating is continued until the evolution of HCl gas has ended (about ½ hour). The toluene and $POCl_3$ are removed by evaporation to leave a viscous brown residual oil (2.5 g), which is then dissolved in methanol (20 cc). The resulting solution is stirred and a solution of sodium methylate (0.3 g; 0.0055 mol) in methanol (10 cc) is then added slowly at ambient temperature. The stirring is continued at ambient temperature for 1 hour after addition of the sodium methylate. The precipitate of NaCl is filtered off and methanol is removed by evaporation. The residual oil is purified by chromatography on silica with methylene chloride as the eluant. This gives a viscous yellow oil of methyl 5-[2'-chloro-4'-(trifluoromethyl)phenoxy]-2-nitro-N-(2-chloroethyl)benzimidate (1.4 g; yield 59%) having the formula:

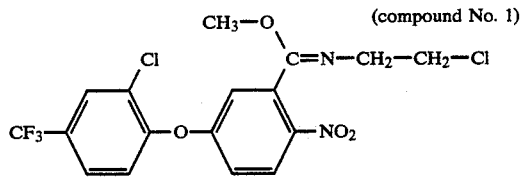

(compound No. 1)

EXAMPLES 2 TO 4

The different compounds Nos. 2 to 4 are prepared by processes analogous to that of Example 1.

EXAMPLE 5

This example illustrates the preparation of compound No. 5.

A solution containing trimethyloxonium tetrafluoroborate (100 g; 0.68 mol) and methylene chloride (2 liters) is prepared. It is stirred and 5-[2'-chloro-4'-(trifluoromethyl)phenoxy]-2-nitrobenzamide (220 g; 0.61 mol) is then added in portions at ambient temperature. The stirring is continued for 24 hours at ambient temperature. The solution is then washed with a 10% aqueous solution of sodium carbonate (cooled beforehand) and dried over sodium sulphate. The methylene chloride is removed by evaporation to leave a yellow solid of methyl 5-[2'-chloro-4'-(trifluoromethyl)phenoxy]-2-nitrobenzimidate (217 g; yield 95%) melting at 46° C. and having the formula:

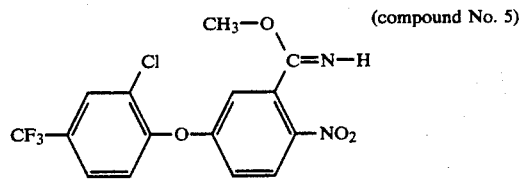

(compound No. 5)

EXAMPLES 6 TO 8

The different compounds Nos. 6 to 8 are prepared by processes analogous to that of Example 5.

EXAMPLES 9 TO 14

The different compounds from 9 to 14 are synthesised by the following general process:

A solution containing compound No. 5 (0.01 mol), triethylamine (1.4 cc) and ethyl ether (20 cc) is prepared. It is stirred and cooled to 0° C. and a solution of acid chloride (of the formula $R^7COCl$) (0.01 mol) in ethyl ether (10 cc) is added dropwise. The stirring is continued for 4 hours at ambient temperature. The precipitate of triethylamine hydrochloride is filtered off and washed with ether. The filtrates are combined, washed with water, dried over sodium sulphate and concentrated; the residual oil is purified by chromatography on silica with a mixture of hexane and ethyl acetate, in respective proportions by volume of 80/20, as the eluant.

EXAMPLES 16 TO 18

The different compounds Nos. 16 to 18 are synthesised by the following general process:

A solution containing compound No. 5 (0.01 mol) and ethyl acetate (5 cc) is prepared and magnesium hydroxide (0.3 g) and water (5 cc) are added thereto. The mixture is stirred vigorously and cooled to 10° C. and chloroformate (of the formula $R^8OCOCl$) (0.011 mol) is introduced dropwise. The stirring is continued for 4 hours at ambient temperature. The excess magnesium hydroxide is destroyed by the addition of a stoichiometric quantity of N HCl. The organic phase is then separated off, washed with a 10% aqueous solution of sodium bicarbonate and then with water, dried over sodium sulphate and concentrated. The residual oil is purified by chromatography on silica with the eluting mixture used in Example 9.

EXAMPLES 19 AND 20

The different compounds Nos. 19 and 20 are prepared by processes analogous to that of Examples 9 to 14, the acid chloride (of the formula $R^7COCl$) being replaced with a sulphamoyl chloride (of the formula $R^5R^4NSO_2Cl$).

EXAMPLES 21 TO 25

The different compounds Nos. 21 to 25 are synthesised by the following general process:

A solution containing compound No. 5 (0.0 mol) and ethyl ether (20 cc) is prepared. It is stirred and a solution of isocyanate (of the formula $R^5NCO$) (0.011 mol) in ethyl ether (10 cc), and also triethylamine (0.1 cc), are added at ambient temperature. The stirring is continued for 120 hours at ambient temperature. The ether is removed by evaporation and the residue is recrystallised or purified by chromatography on silica with the eluting mixture used in Example 9.

EXAMPLES 26 TO 38

The different compounds Nos. 26 to 38 are synthesised by the following general process:

A solution containing phosgene (5.5 g; 0.055 mol) and toluene (120 cc) is prepared. It is stirred and cooled to −20° C. and a solution of compound No. 5 (0.11 mol) in toluene (60 cc) is added dropwise. The stirring is continued while allowing the temperature to rise to +10° C. The precipitate of hydrochloride is filtered off. The toluene filtrate is stirred and cooled to −10° C. A solution of amine (of the formula $R^5R^4NH$) (0.11 mol) in toluene (20 cc) is added dropwise. The stirring is continued for 1 hour at ambient temperature. The precipitate of hydrochloride is filtered off and washed with toluene. The filtrates are combined, washed with water, dried over sodium sulphate and concentrated. The residue is crystallised or purified by chromatography on silica with the eluting mixture used in Example 9.

EXAMPLE 39

This example illustrates the preparation of compound No. 39.

A suspension of 5-[2′-chloro-4′-(trifluoromethyl)-phenoxy]-2-nitrobenzamide (54.1 g; 0.15 mol) and 2,4-bis(4-methoxyphenyl)-1,3-dithia-2,4-diphosphetane-2,4-disulphide (LAWESSON's reagent) (28 g; 0.075 mol) in toluene (250 cc) is prepared. It is heated to 100° C., with stirring, and the heating is continued for 1 hour at this temperature. The toluene is removed by evaporation and the residue is purified by chromatography. This gives a yellow solid of 5-[2′-chloro-4′-(trifluoromethyl)-phenoxy]-2-nitrothiobenzamide (36.4 g; yield 65%) melting at 152° C. and having the formula:

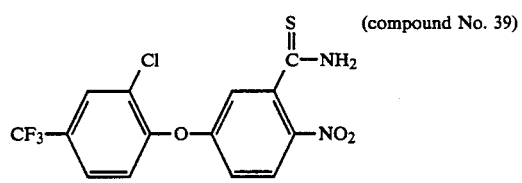
(compound No. 39)

EXAMPLE 40

Compound 40 is prepared from compound No. 39 by a process analogous to that of Example 5. This gives a yellow solid of methyl 5-[2′-chloro-4′-(trifluoromethyl)-phenoxy]-2-nitrothiobenzimidate (yield 98%) melting at 103° C. and having the formula:

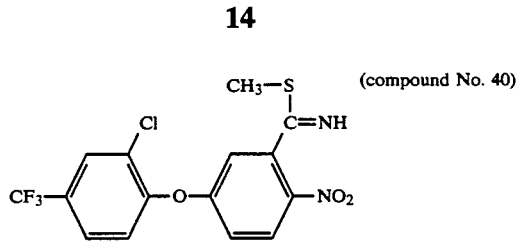
(compound No. 40)

EXAMPLES 41 AND 42

Compounds Nos. 41 and 42 are prepared from compound No. 40 by processes analogous to that of Examples Nos. 21 to 25.

EXAMPLES 43 TO 47

Compounds Nos. 43 to 47 are prepared from compound No. 40 by processes analogous to that of Examples 26 to 38.

EXAMPLE 48

Compound No. 48 is prepared from 5-[3′-chloro-5′-(trifluoromethyl)pyridin-2′-yloxy]-2-nitrobenzamide by a process analogous to that of Example 5. This gives a viscous yellow oil of methyl 5-[3′-chloro-5-(trifluoromethyl)pyridin-2′-yloxy]-2-nitrobenzimidate (yield 32%) having the formula:

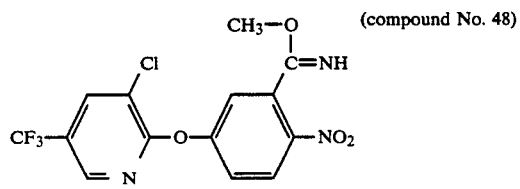
(compound No. 48)

EXAMPLE 49

Compound No. 49 is prepared from compound No. 48 and methyl isocyanate by a process analogous to that of Examples 21 to 25. This gives a white solid of methyl 5-[3′-chloro-5′-(trifluoromethyl)pyridin-2′-yloxy]-2-nitro-N-methylcarbamoylbenzimidate (yield 96%) melting at 134° C. and having the formula:

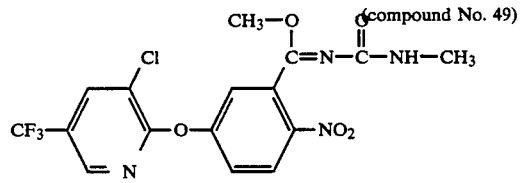
(compound No. 49)

The following compounds can be prepared by processes analogous to those described above:
methyl 5-[2′-chloro-4′-(trifluoromethyl)phenoxy]-2-chloro-N-methylcarbamoylbenzimidate,
methyl 5-[2′-chloro-4′-(trifluoromethyl)phenoxy]-2-bromo-N-methylcarbamoylbenzimidate,
methyl 5-[2′-chloro-4′-(trifluoromethyl)phenoxy]-2-cyano-N-methylcarbamoylbenzimidate,
methyl 5-(2′,4′-dichlorophenoxy)-2-chloro-N-methylcarbamoylbenzimidate,
methyl 5-(2′,4′-dichlorophenoxy)-2-bromo-N-methyl-carbamoylbenzimidate,
methyl 5-(2′,4′-dichlorophenoxy)-2-cyano-N-methylcarbamoylbenzimidate, methyl 5-[2',6'-dichloro-4'-(trifluoromethylphenoxy]-2-chloro-N-methylcarbamoylbenzimidate,
methyl 5-[2'-bromo-4'-(trifluoromethyl)phenoxy]-2-nitro-N-methylcarbamoylbenzimidate,
methyl 5-[2'-iodo-4'-(trifluoromethyl)phenoxy]-2-nitro-N-methylcarbamoylbenzimidate,
methyl 5-[2'-nitro-4'-(trifluoromethyl)phenoxy]-2-nitro-N-methylcarbamoylbenzimidate,
methyl 5-[-2'-cyano-4'-(trifluoromethyl)phenoxy]-2-nitro-N-methylcarbamoylbenzimidate,
methyl 5-[2',4'-bis(trifluoromethyl)phenoxy]-2-nitro-N-methylcarbamoylbenzimidate,
methyl 5-[2',6'-dichloro-4'-(trifluoromethyl)phenoxy]-2-nitro-N-methylcarbamoylbenzimidate,
methyl 5-[2'-chloro-6'-fluoro-4'-(trifluoromethyl)phenoxy]-2-nitro-N-methylcarbamoylbenzimidate,
methyl 5-[2',3',6'-trichloro-4'-(trifluoromethyl)phenoxy]-2-nitro-N-methylcarbamoylbenzimidate,
methyl 5-[2'-nitro-6'-chloro-4'-(trifluoromethyl)phenoxy]-2-nitro-N-methylcarbamoylbenzimidate,
methyl 5-[2',3',5',6'-tetrafluoro-4'-(trifluoromethyl)phenoxy]-2-nitro-N-methylcarbamoylbenzimidate,
methyl 5-[2'-(trifluoromethyl)-4'-chlorophenoxy]-2-nitro-N-methylcarbamoylbenzimidate,
methyl 5-(2'-methyl-4'-chlorophenoxy)-2-nitro-N-methylcarbamoylbenzimidate,
methyl 5-(2'-nitro-4'-chlorophenoxy)-2-nitro-N-methylcarbamoylbenzimidate,
methyl 5-(2',4',6'-trichlorophenoxy)-2-nitro-N-methylcarbamoylbenzimidate,
methyl 5-(2',4'-dichloro-6'-fluorophenoxy)-2-nitro-N-methylcarbamoylbenzimidate,
methyl 5-(2',3',4'-trichlorophenoxy)-2-nitro-N-methylcarbamoylbenzimidate,
methyl 5-(2',4',5'-trichlorophenoxy)-2-nitro-N-methylcarbamoylbenzimidate,
methyl 5-(2',3',4',6'-tetrachlorophenoxy)-2-nitro-N-methylcarbamoylbenzimidate,
methyl 5-(2'-chloro-4'-bromophenoxy)-2-nitro-N-methylcarbamoylbenzimidate,
methyl 5-(2',4'-dibromophenoxy)-2-nitro-N-methylcarbamoylbenzimidate,
methyl 5-(2',4',6'-tribromophenoxy)-2-nitro-N-methylcarbamoylbenzimidate,
methyl 5-(2'-chloro-4'-fluorophenoxy)-2-nitro-N-methylcarbamoylbenzimidate,
methyl 5-(2'-chloro-4'-methylphenoxy)-2-nitro-N-methylcarbamoylbenzimidate,
methyl 5-(2'-nitro-4'-methylphenoxy)-2-nitro-N-methylcarbamoylbenzimidate,
methyl 5-(2',3',6'-trichloro-4'-methylphenoxy)-2-nitro-N-methylcarbamoylbenzimidate,
methyl 5-(2'-chloro-4'-ethylphenoxy)-2-nitro-N-methylcarbamoylbenzimidate,
methyl 5-(2',6'-dichloro-4'-ethylphenoxy)-2-nitro-N-methylcarbomylbenzimidate,
methyl 5-(2',3',5',6'-tetrafluoro-4'-ethylphenoxy)-2-nitro-N-methylcarbamoylbenzimidate,
methyl 5-(3',5'-dichlorophenoxy)-2-nitro-N-methylcarbamoylbenzimidate,
methyl 5-[2'-chloro-4'-(trifluoromethyl)phenoxy]-2-nitro-N-methyoxysulphonylbenzimidate,
methyl 5-[2'-chloro-4'-(trifluoromethyl)phenoxy]-2-nitro-N-(methoxycarbonylmethyl)oxycarbonylbenzimidate,
methyl 5-[2'-chloro-4'-(trifluoromethyl)phenoxy]-2-nitro-N-(1-methoxycarbonylethyl)oxycarbonylbenzimidate (R enantiomer),
methyl 5-[2'-chloro-4'-(trifluoromethyl)phenoxy]-2-nitro-N-(1-methoxycarbonylethyl)oxycarbonylbenzimidate (S enantiomer),
methyl 5-[2'-chloro-4'-(trifluoromethyl)phenoxy]-2-nitro-N-formylbenzimidate,
methyl 5-[2'-chloro-4'-(trifluoromethyl)phenoxy]-2-nitro-N-cyanobenzimidate,
methyl 5-[2'-chloro-4'-(trifluoromethyl)phenoxy]-2-nitro-N-dimethylaminobenzimidate,
methyl 5-[2'-chloro-4'-(trifluoromethyl)phenoxy]-2-nitro-N-chlorobenzimidate,
methyl 5-[2'-chloro-4'-(trifluoromethyl)phenoxy]-2-nitro-N-(O,O-dimethylphosphono)benzimidate,
methyl 5-[2'-chloro-4'-(trifluoromethyl)phenoxy]-2-nitro-N-(O,O-diethylphosphono)benzimidate,
methyl 5-[2'-chloro-4'-(trifluoromethyl)phenoxy]-2-nitro-N-phosphonobenzimidate,
methyl 5-[2'-chloro-4'-(trifluoromethyl)phenoxy]-2-nitro-N-thiocarbamoylbenzimidate,
methyl 5-[2'-chloro-4'-(trifluoromethyl)phenoxy]-2-nitro-N-methylthiocarbomoylbenzimidate,
methyl 5-[2'-chloro-4'-(trifluoromethyl)phenoxy]-2-nitro-N-ethylthiocarbamoylbenzimidate,
methyl 5-[2'-chloro-4'-(trifluoromethyl)phenoxy]-2-nitro-N-dimethylthiocarbamoylbenzimidate,
methyl 5-[3'-chloro-5'-(trifluoromethyl)pyridin-2'-yloxy]-2-nitro-N-carbamoylbenzimidate,
methyl 5-[3'-chloro-5'-(trifluoromethyl)pyridin-2'-yloxy]-2-nitro-N-ethylcarbamoylbenzimidate,
methyl 5-[3'-chloro-5'-(trifluoromethyl)pyridin-2'-yloxy]-2-nitro-N-dimethylcarbamoylbenzimidate,
methyl 5-[5'-(trifluoromethyl)pyridin-2'-yloxy]-2-nitro-N-carbamoylbenzimidate,
methyl 5-[5'-(trifluoromethyl)pyridin-2'-yloxy]-2-nitro-N-methylcarbamoylbenzimidate,
methyl 5-[5'-(trifluoromethyl)pyridin-2'-yloxy]-2-nitro-N-ethylcarbamoylbenzimidate,
methyl 5-[5'-(trifluoromethyl)pyridin-2'-yloxy]-2-nitro-N-dimethylcarbamoylbenzimidate,
methyl 5-(2',4'-dichlorophenoxy)-2-nitro-N-dimethylcarbamoylbenzimidate,
n-propyl 5-[2'-chloro-4'-(trifluoromethyl)phenoxy]-2-nitro-N-methylcarbamoylbenzimidate,
isopropyl 5-[2'-chloro-4'-(trifluoromethyl)phenoxy]-2-nitro-N-methylcarbamoylbenzimidate,
2-chloroethyl 5-[2'-chloro-4'-(trifluoromethyl)phenoxy]-2-nitro-N-methylcarbamoylbenzimidate,
2-methoxyethyl 5-[2'-chloro-4'-(trifluoromethyl)phenoxy]-2-nitro-N-methylcarbamoylbenzimidate,
2,2,2-trichloroethyl 5-[2'-chloro-4'-(trifluoromethyl)phenoxy]-2-nitro-N-methylcarbamoylbenzimidate,
2,2,2-trifluoroethyl 5-[2'-chloro-4'-(trifluoromethyl)phenoxy]-2-nitro-N-methylcarbamoylbenzimidate,
1-(trifluoromethyl)-2,2,2-trifluoroethyl 5-[2'-chloro-4'-(trifluoromethyl)phenoxy]-2-nitro-N-methylcarbamoylbenzimidate,
benzyl 5-[2'-chloro-4'-(trifluoromethyl)phenoxy]-2-nitro-N-methylcarbamoylbenzimidate,
methoxycarbonylmethyl 5-[2'-chloro-4'-(trifluoromethyl)phenoxy]-2-nitro-N-methylcarbamoylbenzimidate,
ethoxycarbonylmethyl 5-[2'-chloro-4'-(trifluoromethyl)phenoxy]-2-nitro-N-methylcarbamoylbenzimidate,
1-methoxycarbonylethyl 5-[2'-chloro-4'-(trifluoromethyl)phenoxy]-2-nitro-N-methylcarbamoylbenzimidate, (R,S), 1-ethoxycarbonylethyl 5-[2'-chloro-4'-(trifluoromethyl)phenoxy]-2-nitro-N-methylcarbamoylbenzimidate, (R,S),
allyl 5-[2'-chloro-4'-(trifluoromethyl)phenoxy]-2-nitro-N-methylcarbamoylbenzimidate,
propargyl 5-[2'-chloro-4'-(trifluoromethyl)phenoxy]-2-nitro-N-methylcarbamoylbenzimidate,
methoxycarbonyl 5-[2'-chloro-4'-(trifluoromethyl)phenoxy]-2-nitro-N-methylcarbamoylthiobenzimidate,
ethoxycarbonylmethyl 5-[2'-chloro-4'-(trifluoromethyl)phenoxy]-2-nitro-N-methylcarbamoylthiobenzimidate,
1-methoxycarbonylethyl 5-[2'-chloro-4'-(trifluoromethyl)phenoxy]-2-nitro-N-methylcarbamoylthiobenzimidate, (R,S),
1-ethoxycarbonylethyl 5-[2'-chloro-4'-(trifluoromethyl)phenoxy]-2-nitro-N-methylcarbamoylthiobenzimidate, (R,S),
5-[2'-chloro-4'-(trifluoromethyl)phenoxy]-2-nitrobenzamidine,
5-[2'-chloro-4'-(trifluoromethyl)phenoxy]-2-nitro-N-methylbenzamidine,
5-[2'-chloro-4'-(trifluoromethyl)phenoxy]-2-nitro-N,N-dimethylbenzamidine,
5-[2'-chloro-4'-(trifluoromethyl)phenoxy]-2-nitrobenzamidoxime,
5-[2'-chloro-4'-(trifluoromethyl)phenoxy]-2-nitro-O-(methoxycarbonylmethyl)benzamidoxime,
5-[2'-chloro-4'-(trifluoromethyl)phenoxy]-2-nitro-O-(1-methoxycarbonylethyl)benzamidoxime (R,S),
5-[2'-chloro-4'-(trifluoromethyl)phenoxy]-2-nitro-N-methylcarbamoylbenzamidine,
5-[2'-chloro-4'-(trifluoromethyl)phenoxy]-2-nitro-N-methylcarbamoyl-N'-methylbenzamidine,
5-[2'-chloro-4'-(trifluoromethyl)phenoxy]-2-nitro-N-methylcarbamoyl-N',N'-dimethylbenzamidine,
5-[2'-chloro-4'-(trifluoromethyl)phenoxy]-2-nitro-N-methylcarbamoyl-O-(methoxycarbonylmethyl)benzamidoxime,
5-[2'-chloro-4'-(trifluoromethyl)phenoxy]-2-nitro-N-methylcarbamoyl-O-(1-methoxycarbonylethyl)benzamicoxime (R,S),
5-[2'-chloro-4'-(trifluoromethyl)phenoxy]-2-nitro-N-methylcarbamoylbenzamidoxime,
methyl 5-[3'-chloro-5'-(trifluoromethyl)pyridin-2'-yloxy]-2-nitro-N-methylcarbamoylthiobenzimidate,
methyl 5-[3'-chloro-5'-(trifluoromethyl)pyridin-2'-yloxy]-2-nitro-N-ethylcarbamoylthiobenzimidate,
methyl 5-[3'-chloro-5'-(trifluoromethyl)pyridin-2'-yloxy]-2-nitro-N-carbamoylthiobenzimidate,
methyl 5-[3'-chloro-5'-(trifluoromethyl)pyridin-2'-yloxy]-2-nitro-N-dimethylcarbamoylthiobenzimidate,
methyl 5-[5'-(trifluoromethyl)pyridin-2'-yloxy]-2-nitro-N-methylcarbamoylthiobenzimidate,
methyl 5-[5'-(trifluoromethyl)pyridin-2'-yloxy]-2-nitro-N-ethylcarbamoylthiobenzimidate,
methyl 5-[5'-(trifluoromethyl)pyridin-2'-yloxy]-2-nitro-N-carbamoylthiobenzimidate and
methyl 5-[5'-(trifluoromethyl)pyridin-2'-yloxy]-2-nitro-N-dimethylcarbamoylthiobenzimidate.

EXAMPLE 50

Herbicidal application in the pre-emergence treatment of plant species

A number of seeds are sown in 9×9×9 cm pots filled with light agricultural earth, the number being determined as a function of the plant species and the size of the seed.

The pots are treated by spraying with a quantity of spraying mixture which corresponds to a volume application dose of 500 liters/ha and containing the active ingredients at the desired concentration.

The treatment with the spraying mixture is thus carried out on seeds not covered with earth (the term "spraying mixture" is generally used to designate the compositions diluted with water, such as they are applied to the plants).

The spraying mixture used for the treatment is an aqueous suspension of the active ingredient containing 0.1% by weight of Cemulsol NP 10 (a surface-active agent consisting of an ethylene oxide/alkylphenol condensate, in particular an ethylene oxide/nonylphenol condensate) and 0.04% by weight of Tween 20 (a surface-active agent consisting of an oleate of an ethylene oxide/sorbitol condensate).

This suspension was obtained by mixing the ingredients and grinding them in a microniser so as to give an average particle size of less than 40 microns.

According to the concentration of active ingredient in the spraying mixture, the dose of active ingredient applied was 0.125 to 2 kg/ha.

After the treatment, the seeds are covered with an approximately 3 mm thick layer of earth.

The pots are then placed in troughs intended to receive the moistening water by sub-irrigation, and are kept for 21 days at ambient temperature under 70% relative humidity.

After 21 days, the number of living plants in the pots treated with the spraying mixture containing the active ingredient to be tested, and the number of living plants in a control pot treated under the same conditions, but by means of a spraying mixture not containing active ingredient, are counted. The percentage destruction of the treated plants relative to the untreated control is thus determined. A percentage destruction equal to 100% indicates that there has been complete destruction of the plant species in question, and a percentage of 0% indicates that the number of living plants in the treated pot is identical to that in the control pot. The results obtained in this Example 50 are shown in Table (III).

EXAMPLE 51

Herbicidal application in the post-emergence treatment of plant species

A number of seeds are sown in 9×9×9 cm pots filled with light agricultural earth, the number being determined as a function of the plant species and the size of the seed.

The seeds are then covered with an approximately 3 mm thick layer of earth and the seed is left to germinate until it produces a plantlet at the appropriate stage. The treatment stage for graminaceous plants is the stage of "second leaf forming". The appropriate stage for soya is the stage of "first trifoliate leaf open". The treatment stage for other dicotyledons is the stage of "cotyledons open, first true leaf developing".

The pots are then treated by spraying with a quantity of spraying mixture which corresponds to a volume application dose of 500 liters/ha and containing the active ingredient at the desired concentration.

The spraying mixture was prepared in the same manner as in Example 50.

According to the concentration of active ingredient in the spraying mixture, the dose of active ingredient applied was 0.125 to 2 kg/ha.

The treated pots are then placed in troughs intended to receive the moistening water by sub-irrigation, and are kept for 21 days at ambient temperature under 70% relative humidity.

After 21 days, the results are accessed as in Example 50. The results obtained in this Example 51 are shown in Table (III).

The tests carried out thus show the remarkably advantageous properties of the compounds according to the invention for pre-emergence and post-emergence treatments of crops, especially soya and cereals. In the case of soya, the activity of the compounds is particularly advantageous if this crop is infested with dicotyledon weeds such as Abutilon, Xanthiun and Ipomea.

For their use in practice, the compounds according to the invention are rarely employed by themselves. Most frequently, these compounds form part of compositions. These compositions, which can be used as herbicides, contain, as the active ingredient, a compound according to the invention such as described above, in association with solid or liquid carriers which are acceptable in agriculture and surface-active agents which are also acceptable in agriculture. The customary inert carriers and the customary surface-active agents can be used in particular. These compositions also form part of the invention.

These composition can also contain all kinds of other ingredients such as e.g. protective colloids, adhesives, thickeners, thixotropic agents, penetrating agents, stabilisers, sequestering agents and the like, as well as other known active ingredients having pesticidal properties (in particular insecticidal, fungicidal or herbicidal properties) or properties which regulate plant growth. More generally, the compounds used in the invention can be used in association with any solid or liquid additives corresponding to the usual formulation techniques.

The use doses of the compounds used in the invention can vary within wide limits, especially according to the nature of the adventitious plants to be eliminated and the usual degree of infestation of the crops by these adventitious plants.

In general, the compositions according to the invention usually contain from 0.05 to about 95% (by weight) of one or more active ingredients according to the invention, from 1% to about 95% of one or more solid or liquid carries and, if appropriate, from 0.1 to about 20% of one or more surface-active agents.

As already stated, the compounds of the invention are generally used in association with carriers and, if appropriate, surface-active agents.

In the present account, the term "carrier" is understood as meaning a natural or synthetic, organic or inorganic substance with which the active ingredient is associated in order to facilitate its application to the plant, to seeds or to the soil. This carrier is therefore generally inert and it must be acceptable in agriculture, especially on the plant treated. The carrier can be solid (clays, natural or synthetic silicates, silica, resins, waxes, solid fertilisers, or the like) or liquid (water; alcohol, in particular butanol; ester, in particular methylglycol acetate; ketones, in particular cyclohexanone and isophorone; petroleum fractions, aromatic hydrocarbons, in particular xylenes, or paraffinic hydrocarbons; aliphatic chlorohydrocarbons, in particular trichloroethane, or aromatic chlorohydrocarbons, in particular chlorobenzenes; water-soluble solvents such as dimethylformamide, dimethyl sulphoxide or N-methylpyrrolidone; liquefied gases, or the like).

The surface-active agent ca be an emulsifying, dispersing or wetting agent of ionic or non-ionic type or a mixture of such surface-active agents. Examples which may be mentioned are polyacrylic acid salts, lignosulphonic acid salts, phenolsulphonic or naphthalenesulfonic acid salts, polycondensates or ethylene oxide with fatty alcohols, fatty acids or fatty amines, substituted phenols (in particular alkylphenols or arylphenols), salts of sulphosuccinic acid esters, taurine derivatives (in particular alkyltaurates), phosphoric acid esters of condensates of ethylene oxide with alcohols or phenols, fatty acid esters or polyols, and derivatives of the above compounds which contain sulphate, sulphonate and phosphate groups. The presence of at least one surface-active agent is generally essential if the active ingredient and/or the inert carrier are not soluble in water and if the vehicle of application is water.

For their application, the compounds of the formula (I) are therefore generally in the form of compositions; these compositions according to the invention are themselves in a fairly wide variety of solid or liquid forms.

Forms of solid compositions which may be mentioned are dusting powders (with a content of compound of the formula (I) which can range up to 100%) and granules, especially those obtained by extrusion, by compaction, by the impregnation of a granular carrier or by the conversion of a powder to granules (the content of compound of the formula (I) in these granules being between 0.5 and 80% for the latter cases).

As forms of liquid compositions or compositions intended to be made up into liquid compositions on application, there may be mentioned solutions, in particular emulsifiable concentrates, emulsions, flowables, aerosols, wettable powders (or spraying powders), dry flowables and pastes.

The emulsifiable or soluble concentrates also most frequently comprise 10 to 80% of active ingredient and the emulsions or solutions ready for application contain 0.01 to 20% of active ingredient. In addition to the solvent, and where necessary, the emulsifiable concentrates can contain 2 to 20% of suitable additives such as stabilisers, surface-active agents, penetrating agents, corrosion inhibitors, colorants and adhesives.

Emulsions of any desired concentration, which are particularly suitable for application to plants, can be obtained from these concentrates by dilution with water.

The compositions of a few emulsifiable concentrates are now given as examples:

| | |
|---|---|
| active ingredient | 250 g |
| ethylene oxide/alkylphenol condensate | 30 g |
| calcium alkylarylsulphonate | 50 g |
| petroleum distillation cut distilling at between 160 and 185° C. | 670 g |

Another formulation:

| | |
|---|---|
| active ingredient | 350 g |
| ethylene oxide/castor oil condensate | 60 g |
| sodium alkylarylsulphonate | 40 g |
| cyclohexanone | 150 g |
| xylene | 400 g |

Another formulation:

| | |
|---|---|
| active ingredient | 400 g |
| ethylene oxide/alkylphenol condensate | 100 g |
| ethylene glycol methyl ether | 250 g |
| aromatic petroleum cut distilling at between 160 and 185° C. | 250 g |

Another formulation:

| | |
|---|---|
| active ingredient | 400 g |
| phosphate of ethylene oxide/tristyrylphenol condensate | 50 g |
| phosphate of ethylene oxide/alkylphenol condensate | 65 g |
| sodium alkylbenzenesulphonate | 35 g |
| cyclohexanone | 300 g |
| aromatic petroleum cut distilling at between 160 and 185° C. | 150 g |

Another formulation:

| | |
|---|---|
| active ingredient | 400 g/liter |
| alkali metal dodecylbenzenesulphonate | 24 g/liter |
| 10:1 ethylene oxide/nonylphenol condensate | 16 g/liter |
| cyclohexanone | 200 g/liter |
| aromatic solvent q.s. | 1 liter |

Another emulsifiable concentrate formulation uses the following:

| | |
|---|---|
| active ingredient | 250 g |
| epoxidised vegetable oil | 25 g |
| mixture of an alkylarylsulphonate and an ether of polyglycol and fatty alcohols | 100 g |
| dimethylformamide | 50 g |
| xylene | 575 g |

The flowables, which can be applied by spraying, are prepared so as to give a stable fluid product which does not form a deposit (fine grinding), and they usually contain from 10 to 75% of active ingredient, from 0.5 to 15% of surface-active agents, from 0.1 to 10% of thixotropic agents, from 0 to 10% of suitable additives such as antifoams, corrosion inhibitors, stabilisers, penetrating agents and adhesives, and, as the carrier, water or an organic liquid in which the active ingredient is sparingly soluble or insoluble; certain organic solids, or inorganic salts, can be dissolved in the carrier in order to assist in preventing sedimentation or to act as antifreeze agents for the water.

The composition of a flowable is now given as an example:

| | |
|---|---|
| active ingredient | 500 g |
| phosphate of ethylene oxide/tristyrylphenol condensate | 50 g |
| ethylene oxide/alkylphenol condensate | 50 g |
| sodium polycarboxylate | 20 g |
| ethylene glycol | 50 g |
| organopolysiloxane oil (antifoam) | 1 g |
| polysaccharide | 1.5 g |
| water | 316.5 g |

The wettable powders (or spraying powders) are usually prepared so as to contain 20 to 95% of active ingredient, and they usually contain, in addition to the solid carrier, from 0 to 5% of a wetting agent, from 3 to 10% of a dispersing agent and, where necessary, from 0 to 10% of one or more stabilisers and/or other additives such as penetrating agents, adhesives, anti-caking agents, colorants and the like.

Various compositions of wettable powders are now given as examples:

| | |
|---|---|
| active ingredient | 50% |
| calcium lignosulphonate (deflocculant) | 5% |
| isopropylnaphthalenesulphonate (anionic wetting agent) | 1% |
| anti-caking silica | 5% |
| kaolin (filler) | 39% |

Another example of a wettable powder, containing 80% of active ingredient, is given below:

| | |
|---|---|
| active ingredient | 80% |
| sodium alkylnaphthalenesulphonate | 2% |
| sodium lignosulphonate | 2% |
| anti-caking silica | 3% |
| kaolin | 13% |

Another example of a wettable powder is given below:

| | |
|---|---|
| active ingredient | 50% |
| sodium alkylnaphthalenesulphonate | 2% |
| low-viscosity methylcellulose | 2% |
| diatomaceous earth | 46% |

Another exmaple of a wettable powder is given below:

| | |
|---|---|
| active ingredient | 90% |
| sodium dioctyl-sulphosuccinate | 0.2% |
| synthetic silica | 9.8% |

Another composition of a spraying powder, containing 40% of active ingredient, uses the following constituents:

| | |
|---|---|
| active ingredient | 400 g |
| sodium lignosulphonate | 50 g |
| sodium dibutylnaphthalenesulphonate | 10 g |
| silica | 540 g |

Another composition of a spraying powder, containing 25% of active ingredient, uses the following constituents:

| | |
|---|---|
| active ingredient | 250 g |
| ethylene oxide/isooctylphenoxyethanol condensate | 25 g |
| mixture of equal parts by weight of Champagne chalk and hydroxyethylcellulose | 17 g |
| sodium aluminosilicate | 543 g |
| kieselguhr | 165 g |

Another composition of a spraying powder, containing 10% of active ingredient, uses the following constituents:

| | |
|---|---|
| active ingredient | 100 g |
| mixture of sodium salts of saturated | 30 g |

| | |
|---|---|
| fatty acid sulphates | |
| naphthalenesulphonic acid/formaldehyde condensate | 50 g |
| kaolin | 820 g |

To obtain these spraying powders or wettable powders, the active ingredients are intimately mixed with the additional substances in suitable mixers or the porous filler is impregnated with the molten active ingredient and the product is ground in mills or other suitable grinders. This gives spraying powders of advantageous wettability and suspendability; they can be suspended in water at any desired concentration and this suspension can be used very advantageously, in particular for application to the leaves of plants.

The dry flowables (more exactly, these are granules readily dispersible in water) have a composition substantially similar to that of the wettable powders. They can be prepared by granulation of formulations described for the wettable powders, either by a wet method (bringing the finely divided active ingredient into contact with the inert filler and with a small quantity of water, e.g. 1 to 20%, or a small quantity of aqueous solution of dispersing agent or binder, followed by drying and sieving), or by a dry method (compaction followed by grinding and sieving).

A formulation of a dry flowable is now given as an example:

| | |
|---|---|
| active ingredient | 800 g |
| sodium alkylnaphthalenesulphonate | 20 g |
| sodium methylenebisnaphthalenesulphonate | 80 g |
| kaolin | 100 g |

Instead of the wettable powders, it is possible to produce pastes. The conditions and modified ways of producing and using these pastes are similar to those of the wettable powders or spraying powders.

As already stated, the aqueous emulsions and dispersions, e.g. compositions obtained by diluting a wettable powder or an emulsifiable concentrate according to the invention with water, are included within the general scope of the compositions which can be used in the present invention. The emulsions can be of the water-in-oil or oil-in-water type and can have a thick consistency such as that of a "mayonnaise".

All these aqueous emulsions or dispersions, or spraying mixtures, can be applied by any suitable means to the crops in which weeds are to be destroyed, mainly by spraying, at doses which are generally of the order of 100 to 1200 liters of spraying mixture per hectare.

The granules, which are intended to be placed on the soil, are usually prepared so as to have dimensions of between 0.1 and 2 mm, and they can be manufactured by agglomeration or impregnation. Preferably, the granules contain 1 to 25% of active ingredient and 0 to 10% of additives such as stabilisers, slow-release modifiers, binders and solvents.

One example of the composition of granules uses the following constituents:

| | |
|---|---|
| active ingredient | 50 g |
| propylene glycol | 25 g |
| boiled linseed oil | 50 g |
| clay (particle size: 0.3 to 0.8 mm) | 910 g |

As indicated above, the invention also relates to a process for destroying weeds in crops, especially cereals such as wheat, and also soya, wherein an effective quantity, which is non-phytotoxic towards the crop in question, of at least one of the compounds according to the invention is applied to the plants and/or to the soil in the area in which weeds are to be destroyed. In practice, these compounds are used in the form of the herbicidal compositions according to the invention which have been described above. Quantities of active ingredient ranging from 0.01 to 5 kg/ha, preferably from 0.1 to 2 kg/ha, generally give good results, it being understood that the choice of the quantity of active ingredient to be used depends on the severity of the problem to be solved, the climatic conditions and the crop in question. The treatment can be carried out as a pre-emergence treatment of the crops and adventitious plants, or as a pre-sowing treatment of the crops, with incorporation into the soil (this incorporation is thus an additional operation to the treatment process of the invention), or as a post-emergence treatment. Other methods of carrying out the treatment process according to the invention can also be used: thus, it is possible to apply the active ingredient to the soil, with or without incorporation, before planting out a crop.

The treatment process of the invention is equally applicable to the case of annual crops as to the case of perennial crops; in the latter case, it is preferred to apply the active ingredients of the invention in a localised manner, e.g. between the rows of the said crops.

TABLE (1)

| Compound No. | X | W | $X^2R^3$ | $R^2$ | Yield (%) | M.p. (°C.) | Spectral characteristics IR or NMR |
|---|---|---|---|---|---|---|---|
| 1 | $CF_3$ | $NO_2$ | $OCH_3$ | $CH_2CH_2Cl$ | 59 | Oil | 1869, 1583, 1530, 1323, 1130, 1080 (IR) |
| 2 | $CF_3$ | $NO_2$ | $OCH_3$ | $CH_2CH=CH_2$ | 29 | Oil | 3.73–3.86 (NMR) |
| 3 | $CF_3$ | $NO_2$ | $OCH_3$ | $SO_2F$ | 26 | 53 | |
| 4 | $CF_3$ | $NO_2$ | $OCH_3$ | $SO_2OC_2H_5$ | 45 | 70 | |
| 5 | $CF_3$ | $NO_2$ | $OCH_3$ | H | 95 | 46 | |
| 6 | Cl | $NO_2$ | $OCH_3$ | H | 63 | 107 | |
| 7 | $CF_3$ | Cl | $OCH_3$ | H | 51 | Oil | 1650, 1575, 1323, 1125, 1080 (IR) |
| 8 | $CF_3$ | $NO_2$ | $OC_2H_5$ | H | 90 | Oil | 1650, 1582, 1530, 1322, 1128, 1080 (IR) |
| 9 | $CF_3$ | $NO_2$ | $OCH_3$ | $COCH_3$ | 74 | 117 | |
| 10 | $CF_3$ | $NO_2$ | $OCH_3$ | $COC_2H_5$ | 93 | 53 | |
| 11 | $CF_3$ | $NO_2$ | $OCH_3$ | $CO(CH_2)_2CH_3$ | 69 | Oil | 1702, 1674, 1586, 1532, 1325, 1129, 1081 (IR) |
| 12 | $CF_3$ | $NO_2$ | $OCH_3$ | $COCH(CH_3)_2$ | 49 | Oil | 1.04–2.50–3.92 (NMR) |

TABLE (1)-continued

| Compound No. | X | W | X²R³ | R² | Yield (%) | M.p. (°C.) | Spectral characteristics IR or NMR |
|---|---|---|---|---|---|---|---|
| 13 | CF₃ | NO₂ | OCH₃ | COCHCL₂ | 59 | Oil | 1715, 1696, 1640, 1585, 1530, 1322, 1128, 1080 (IR) |
| 14 | CF₃ | NO₂ | OCH₃ | COCCl₃ | 82 | Oil | 1718, 1640, 1585, 1530, 1322, 1128, 1080 (IR) |
| 16 | CF₃ | NO₂ | OCH₃ | COOC₂H₅ | 64 | Oil | 1730, 1670, 1586, 1531, 1323, 1134, 1081 (IR) |
| 17 | CF₃ | NO₂ | OCH₃ | COOCH(CH₃)COOCH₃ (R,S) | 50 | Oil | 1755, 1730, 1670, 1584, 1530, 1322, 1128, 1079 (IR) |
| 18 | CF₃ | NO₂ | OCH₃ | COOCH(CH₃)COOC₂H₅ (R,S) | 60 | Oil | 1735 broad, 1668, 1581, 1529, 1320, 1128, 1078, (IR) |
| 19 | CF₃ | NO₂ | OCH₃ | SO₂NH₂ | 66 | 118 | |
| 20 | CF₃ | NO₂ | OCH₃ | SO₂NHCH₃ | 41 | 109 | |
| 21 | CF₃ | NO₂ | OCH₃ | CONHC₂H₅ | 59 | 126 | |
| 22 | CF₃ | NO₂ | OC₂H₅ | CONHCH₃ | 58 | 82 | |
| 23 | CF₃ | NO₂ | OC₂H₅ | CONHC₂H₅ | 82 | 90 | |
| 24 | Cl | NO₂ | OCH₃ | CONHCH₃ | 64 | 136 | |
| 25 | Cl | NO₂ | OCH₃ | CONHC₂H₅ | 33 | 87 | |
| 26 | CF₃ | NO₂ | OCH₃ | CONH₂ | 45 | 120 | |
| 27 | Cl | NO₂ | OCH₃ | CONH₂ | 78 | 149 | |
| 28 | CF₃ | NO₂ | OCH₃ | CONHCH₃ | 55 | 116 | |
| 29 | CF₃ | NO₂ | OCH₃ | CONH(CH₂)₂CH₃ | 30 | Oil | 0.75–3.90-132–3.04 (NMR) |
| 30 | CF₃ | NO₂ | OCH₃ | CONHCH(CH₃)₂ | 30 | 95 | |
| 31 | CF₃ | NO₂ | OCH₃ | CONH—◁ | 34 | 135 | |
| 32 | CF₃ | NO₂ | OCH₃ | CONHCH₂CH=CH₂ | 44 | 94 | |
| 33 | CF₃ | NO₂ | OCH₃ | CONHCH₂C≡CH | 48 | 70 | |
| 34 | CF₃ | NO₂ | OCH₃ | CONH(CH₂)₃CH₃ | 40 | 78 | |
| 35 | CF₃ | NO₂ | OCH₃ | CON(CH₃)₂ | 31 | 120 | |
| 36 | CF₃ | NO₂ | OCH₃ | CON(CH₃)(C₂H₅) | 63 | Oil | 1675, 1653, 1587, 1535, 1325, 1130, 1083 (IR) |
| 37 | CF₃ | NO₂ | OCH₃ | CON(CH₃)(OCH₃) | 28 | Oil | 3.13–3.63–3.97 (NMR) |
| 38 | CF₃ | NO₂ | OCH₃ | CON(C₂H₅)₂ | 26 | Oil | 1669, 1645, 1582, 1529, 1434, 1127, 1080 (IR) |
| 41 | CF₃ | NO₂ | SCH₃ | CONHCH₃ | 81 | 96 | |
| 42 | CF₃ | NO₂ | SCH₃ | CONHC₂H₅ | 80 | 82 | |
| 43 | CF₃ | NO₂ | SCH₃ | CONH₂ | 39 | 143 | |
| 44 | CF₃ | NO₂ | SCH₃ | CONH—CH₂—CH=CH₂ | 47 | Oil | 1675, 1620, 1582, 1529, 1325, 1130, 1081 (IR) |
| 45 | CF₃ | NO₂ | SCH₃ | CON(CH₃)₂ | 31 | Oil | 1658, 1618, 1580, 1528, 1322, 1127, 1079 (IR) |
| 46 | CF₃ | NO₂ | SCH₃ | CON(CH₃)(C₂H₅) | 37 | Oil | 1657, 1620, 1582, 1526, 1325, 1129, 1081 (IR) |
| 47 | CF₃ | NO₂ | SCH₃ | CON(CH₃)(OCH₃) | 27 | Oil | 1672, 1620, 1580, 1530, 1322, 125, 1079 (IR) |

TABLE (II)

| | American name | Latin name | Abbreviation |
|---|---|---|---|
| Crop | Wheat | | WHE |
| | Soybean | | SOY |

TABLE (II)-continued

| American name | Latin name | Abbreviation |
|---|---|---|
| Weeds Barnyard grass | Echinochloa crus-galli | ECH |
| Velvet leaf | Abutilon theophrasti | ABU |
| Cocklebur | Xanthium pennsylvanicum | XAN |

TABLE (II)-continued

| American name | Latin name | Abbreviation |
|---|---|---|
| Wild mustard | Sinapis arvensis | SIN |
| Morning glory (annual) | Ipomea purpurea | IPO |
| Rye-grass | Lolium multi florum | LOL |

TABLE (III)

| Compound No. | Doses in kg/ha | PRE-EMERGENCE TREATMENT ||||||||| POST-EMERGENCE TREATMENT |||||||| |
|---|---|---|---|---|---|---|---|---|---|---|---|---|---|---|---|---|---|
| | | ECH | LOL | ABU | IPO | SIN | XAN | WHE | SOY | ECH | LOL | ABU | IPO | SIN | XAN | WHE | SOY |
| 1 | 2 | 90 | 98 | 100 | 0 | 100 | — | 0 | 0 | 100 | 98 | 100 | 100 | 100 | — | 20 | 0 |
| | 0.5 | 40 | 30 | 80 | 0 | 80 | — | 0 | 0 | 98 | 20 | 100 | 80 | 98 | — | 20 | 0 |
| | 0.125 | 0 | 0 | 0 | 0 | 0 | — | 0 | 0 | 30 | 0 | 50 | 80 | 80 | — | 0 | 0 |
| 2 | 2 | 100 | 95 | 100 | 30 | 100 | — | 20 | — | 100 | 100 | 100 | 100 | 100 | — | 30 | 0 |
| | 0.5 | 30 | 60 | 95 | 0 | 100 | — | 0 | — | 100 | 20 | 100 | 100 | 100 | — | 0 | 0 |
| | 0.125 | 0 | 0 | 0 | 0 | 0 | — | 0 | — | 80 | 20 | 80 | 80 | 80 | — | 0 | 0 |
| 3 | 2 | 90 | 20 | 100 | 0 | 100 | — | 0 | 0 | 100 | 30 | 100 | 100 | 100 | — | 0 | 20 |
| | 0.5 | 0 | 0 | 20 | 0 | 50 | — | 0 | 0 | 100 | 20 | 80 | 80 | 80 | — | 0 | 0 |
| | 0.125 | 0 | 0 | 0 | 20 | 0 | — | 0 | 0 | 50 | 0 | 40 | 80 | 60 | — | 0 | 0 |
| 4 | 2 | 80 | 0 | 100 | 0 | 100 | — | 0 | 0 | 40 | 0 | 100 | 100 | 100 | — | 0 | 0 |
| | 0.5 | 0 | 0 | 30 | 0 | 50 | — | 0 | 0 | 0 | 0 | 80 | 100 | 100 | — | 0 | 0 |
| | 0.125 | 0 | 0 | 0 | 0 | 30 | — | 0 | 0 | 0 | 0 | 30 | 80 | 80 | — | 0 | 0 |
| 5 | 2 | 100 | — | 100 | 95 | 100 | 0 | 0 | 0 | 100 | 100 | 100 | 100 | 100 | 100 | 40 | 00 |
| | 0.5 | 98 | — | 100 | 80 | 100 | 0 | 0 | 0 | 100 | 80 | 98 | 100 | 100 | 100 | 20 | 80 |
| | 0.125 | 0 | 0 | 30 | 0 | 30 | 0 | 0 | 0 | 20 | 20 | 90 | 80 | 50 | 50 | 0 | 80 |
| 6 | 2 | 0 | 0 | 100 | 0 | 80 | 0 | 0 | 0 | 60 | 20 | 50 | 80 | 40 | 0 | 0 | 0 |
| | 0.5 | 0 | 0 | 60 | 0 | 20 | 0 | 0 | 0 | 30 | 0 | 30 | 50 | 20 | 0 | 0 | 0 |
| | 0.125 | 0 | 0 | 20 | 0 | 0 | 0 | 0 | 0 | 20 | 0 | 20 | 30 | 20 | 0 | 0 | 0 |
| 7 | 2 | 100 | 90 | 100 | 100 | 100 | 0 | 70 | 0 | 100 | 100 | 100 | 100 | 100 | 50 | 50 | 50 |
| | 0.5 | 40 | 20 | 60 | 30 | 30 | 0 | 0 | 0 | 100 | 80 | 100 | 100 | 95 | 0 | 0 | 30 |
| | 0.125 | 20 | 0 | 20 | 0 | 20 | 0 | 0 | 0 | 98 | 20 | 98 | 80 | 30 | 0 | 0 | 0 |
| 8 | 2 | 100 | 100 | 100 | 70 | 100 | 0 | 50 | 50 | 100 | 100 | 100 | 100 | 100 | 100 | 20 | 30 |
| | 0.5 | 98 | 80 | 100 | 0 | 80 | 0 | 0 | 0 | 100 | 80 | 100 | 100 | 80 | 100 | 0 | 0 |
| | 0.125 | 20 | 0 | 50 | 0 | 0 | 0 | 0 | 0 | 90 | 20 | 100 | 100 | 30 | 20 | 0 | 0 |
| 9 | 2 | 98 | 80 | 100 | 0 | 30 | 0 | 0 | 0 | 100 | 20 | 100 | 90 | 100 | 100 | 0 | 30 |
| | 0.5 | 30 | 0 | 80 | 0 | 80 | 0 | 0 | 0 | 70 | 0 | 90 | 100 | 80 | 0 | 0 | 0 |
| | 0.125 | 0 | 0 | 0 | 0 | 30 | 0 | 0 | 0 | 20 | 0 | 80 | 100 | 20 | 0 | 0 | 0 |
| 10 | 2 | 100 | 80 | 100 | 100 | 100 | 0 | 0 | 0 | 100 | 30 | 100 | 100 | 100 | 50 | 20 | 30 |
| | 0.5 | 20 | 0 | 80 | 20 | 80 | 0 | 0 | 0 | 80 | 0 | 90 | 100 | 95 | 0 | 0 | 0 |
| | 0.125 | 0 | 0 | 20 | 0 | 80 | 0 | 0 | 0 | 30 | 0 | 80 | 100 | 60 | 0 | 0 | 0 |
| 11 | 2 | 95 | 50 | 100 | 90 | 90 | 100 | 0 | 30 | 100 | 30 | 100 | 50 | 100 | 100 | 20 | 30 |
| | 0.5 | 50 | 30 | 95 | 0 | 80 | 50 | 0 | 0 | 60 | 20 | 100 | 50 | 100 | 0 | 0 | 20 |
| | 0.125 | 0 | 0 | 90 | 0 | 80 | 0 | 0 | 0 | 20 | 0 | 20 | 80 | 30 | 0 | 0 | 0 |
| 12 | 2 | 100 | 80 | 100 | 50 | 100 | 70 | 0 | 0 | 100 | 95 | 100 | 100 | 95 | 100 | 20 | 20 |
| | 0.5 | 30 | 20 | 100 | 0 | 90 | 0 | 0 | 0 | 90 | 20 | 90 | 50 | 90 | 50 | 0 | 0 |
| | 0.125 | 0 | 0 | 30 | 0 | 80 | 0 | 0 | 0 | 0 | 0 | 60 | 50 | 20 | 0 | 0 | 0 |
| 13 | 2 | 100 | 100 | 100 | 100 | 100 | 50 | 20 | 0 | 100 | 30 | 100 | 100 | 100 | 30 | 0 | 0 |
| | 0.5 | 100 | 90 | 100 | 30 | 100 | 30 | 0 | 0 | 100 | 20 | 100 | 100 | 100 | 0 | 0 | 0 |
| | 0.125 | 30 | 0 | 0 | 0 | 0 | 0 | 0 | 0 | 50 | 0 | 95 | 30 | 30 | 0 | 0 | 0 |
| 14 | 2 | 100 | 90 | 100 | 30 | 100 | 0 | 20 | 0 | 100 | 30 | 100 | 100 | 100 | 100 | 30 | 0 |
| | 0.5 | 100 | 40 | 100 | 0 | 100 | 0 | 0 | 0 | 100 | 20 | 100 | 90 | 100 | 50 | 0 | 0 |
| | 0.125 | 30 | 0 | 80 | 0 | 0 | 0 | 0 | 0 | 80 | 0 | 90 | 50 | 90 | 30 | 0 | 0 |
| 16 | 2 | 100 | 40 | 100 | 50 | 20 | 0 | 0 | 0 | 100 | 80 | 90 | 100 | 100 | — | 20 | 30 |
| | 0.5 | 30 | 30 | 80 | 0 | 20 | 0 | 0 | 0 | 80 | 30 | 90 | 100 | 100 | — | 20 | 0 |
| | 0.125 | 0 | 0 | 0 | 0 | 0 | 0 | 0 | 0 | 20 | 0 | 80 | 90 | 70 | — | 0 | 0 |
| 17 | 2 | 100 | 70 | 100 | 100 | 100 | 80 | 0 | 80 | 98 | 30 | 100 | 100 | 100 | 100 | 0 | 50 |
| | 0.5 | 100 | 40 | 100 | 100 | 98 | 0 | 50 | 0 | 80 | 10 | 100 | 100 | 100 | 100 | 0 | 40 |
| | 0.125 | 60 | 10 | 100 | 100 | 100 | 0 | 0 | 0 | 50 | 0 | 95 | 100 | 98 | 100 | 0 | 0 |
| 18 | 2 | 98 | 80 | 100 | 100 | 100 | 80 | 30 | 80 | 100 | 40 | 100 | 100 | 98 | 100 | 0 | 20 |
| | 0.5 | 80 | 40 | 100 | 60 | 100 | 0 | 0 | 0 | 98 | 10 | 100 | 100 | 100 | 80 | 0 | 0 |
| | 0.125 | 60 | 0 | 100 | 20 | 100 | 0 | 0 | 20 | 50 | 0 | 90 | 100 | 100 | 70 | 0 | 0 |
| 19 | 2 | 100 | 100 | 100 | 100 | 100 | 80 | 80 | 70 | 100 | 100 | 100 | 100 | 100 | 100 | 50 | 50 |
| | 0.5 | 90 | 98 | 100 | 100 | 100 | 50 | 50 | 30 | 100 | 90 | 80 | 100 | 100 | 80 | 0 | 30 |
| | 0.125 | 60 | 60 | 100 | 50 | 100 | 0 | 0 | 0 | 50 | 20 | 60 | 100 | 100 | 30 | 0 | 0 |
| 20 | 2 | 95 | 100 | 100 | 0 | 100 | 0 | 0 | 0 | 20 | 40 | 98 | 100 | 100 | 20 | 10 | 0 |
| | 0.5 | 30 | 60 | 100 | 0 | 95 | 0 | 0 | 0 | 0 | 0 | 80 | 90 | 90 | 0 | 0 | 0 |
| | 0.125 | 0 | 0 | 95 | 0 | 40 | 0 | 0 | 0 | 0 | 0 | 0 | 40 | 20 | 0 | 0 | 0 |
| 21 | 2 | 100 | 100 | 100 | 100 | 100 | 85 | 85 | 100 | 80 | 70 | 90 | 80 | 100 | 100 | 0 | 20 |
| | 0.5 | 100 | 100 | 100 | 90 | 100 | 60 | 60 | 100 | 60 | 40 | 80 | 80 | 100 | 80 | 0 | 20 |
| | 0.125 | 80 | 80 | 100 | 50 | 100 | 0 | 0 | 0 | 20 | 20 | 60 | 0 | 80 | 20 | 0 | 0 |
| 22 | 2 | 100 | 100 | 100 | 100 | 100 | 100 | 100 | 50 | 100 | 100 | 100 | 100 | 100 | 100 | 50 | 100 |
| | 0.5 | 100 | 100 | 100 | 30 | 100 | 30 | 100 | 0 | 100 | 100 | 100 | 100 | 100 | 100 | 20 | 100 |
| | 0.125 | 98 | 100 | 100 | 0 | 95 | 0 | 20 | 0 | 90 | 95 | 100 | 100 | 98 | 50 | 20 | 70 |
| 23 | 2 | 100 | 100 | 100 | 90 | 100 | 0 | 100 | 0 | 100 | 100 | 100 | 100 | 98 | 100 | 20 | 0 |
| | 0.5 | 100 | 100 | 100 | 30 | 30 | 0 | 30 | 0 | 95 | 100 | 98 | 100 | 30 | 0 | 0 | 0 |
| | 0.125 | 90 | 90 | 90 | 0 | 0 | 0 | 0 | 0 | 90 | 50 | 80 | 100 | 20 | 0 | 0 | 0 |
| 24 | 2 | 100 | 100 | 100 | 50 | 100 | 0 | 80 | 30 | 98 | 98 | 100 | 30 | 0 | 0 | 0 | 30 |

TABLE (III)-continued

| Compound No. | Doses in kg/ha | PRE-EMERGENCE TREATMENT | | | | | | | | POST-EMERGENCE TREATMENT | | | | | | | |
|---|---|---|---|---|---|---|---|---|---|---|---|---|---|---|---|---|---|
| | | ECH | LOL | ABU | IPO | SIN | XAN | WHE | SOY | ECH | LOL | ABU | IPO | SIN | XAN | WHE | SOY |
| | 0.5 | 100 | 100 | 100 | 50 | 100 | 0 | 30 | 30 | 60 | 20 | 50 | 80 | 30 | 0 | 0 | 0 |
| | 0.125 | 95 | 90 | 100 | 0 | 100 | 0 | 0 | 0 | 20 | 0 | 30 | 100 | 20 | 0 | 0 | 0 |
| 25 | 2 | 100 | 100 | 100 | 80 | 100 | 0 | 80 | 100 | 100 | 100 | 100 | 100 | 100 | 0 | 20 | 30 |
| | 0.5 | 100 | 100 | 50 | 100 | 0 | 30 | 30 | 100 | 90 | 90 | 80 | 60 | 0 | 0 | 0 | |
| | 0.125 | 100 | 98 | 100 | 30 | 90 | 0 | 0 | 0 | 80 | 20 | 80 | 30 | 30 | 0 | 0 | 0 |
| 26 | 2 | 100 | 100 | 100 | 100 | 100 | 100 | 100 | 100 | 100 | 100 | 100 | 100 | 100 | 100 | 90 | 100 |
| | 0.5 | 100 | 100 | 100 | 80 | 100 | 50 | 80 | 100 | 100 | 100 | 100 | 100 | 100 | 100 | 80 | 0 |
| | 0.125 | 100 | 100 | 100 | 0 | 100 | 0 | 50 | 0 | 90 | 70 | 100 | 70 | 100 | 100 | 20 | 0 |
| 27 | 2 | 100 | 100 | 100 | 100 | 100 | 0 | 90 | 100 | 98 | 70 | 90 | 100 | 60 | 80 | 0 | 50 |
| | 0.5 | 90 | 98 | 100 | 0 | 100 | 0 | 30 | 50 | 30 | 30 | 90 | 100 | 30 | 0 | 0 | 30 |
| | 0.125 | 80 | 50 | 100 | 0 | 100 | 0 | 0 | 30 | 0 | 0 | 90 | 100 | 20 | 0 | 0 | 0 |
| 28 | 2 | 100 | 100 | 100 | 100 | 100 | 90 | 100 | 100 | 100 | 100 | 100 | 100 | 100 | 100 | 90 | 50 |
| | 0.5 | 100 | 100 | 100 | 100 | 100 | 0 | 98 | 100 | 100 | 100 | 100 | 100 | 100 | 100 | 80 | 30 |
| | 0.125 | 100 | 100 | 100 | 80 | 100 | 100 | 90 | 70 | 80 | 90 | 100 | 100 | 50 | 50 | 20 | 0 |
| 29 | 2 | 90 | 100 | 100 | 50 | 100 | 0 | 50 | 50 | 100 | 100 | 100 | 50 | 100 | 30 | 20 | 20 |
| | 0.5 | 80 | 90 | 100 | 20 | 100 | 0 | 20 | 30 | 95 | 95 | 100 | 50 | 50 | 30 | 10 | 20 |
| | 0.125 | 50 | 40 | 95 | 0 | 50 | 0 | 0 | 0 | 20 | 40 | 30 | 20 | 10 | 0 | 10 | 20 |
| 30 | 2 | 100 | 100 | 100 | 0 | 98 | 0 | 50 | 0 | 100 | 60 | 100 | 50 | 100 | 0 | 0 | 0 |
| | 0.5 | 80 | 80 | 100 | 0 | 50 | 0 | 30 | 0 | 80 | 20 | 30 | 50 | 95 | 0 | 0 | 0 |
| | 0.125 | 30 | 20 | 90 | 0 | 30 | 0 | 0 | 0 | 30 | 0 | 0 | 50 | 30 | 0 | 0 | 0 |
| 31 | 2 | 100 | 100 | 100 | 80 | 100 | 0 | 20 | 0 | 100 | 60 | 100 | 80 | 100 | 30 | 0 | 30 |
| | 0.5 | 100 | 98 | 100 | 0 | 98 | 0 | 0 | — | 40 | 20 | 100 | 80 | 98 | 0 | 0 | 0 |
| | 0.125 | 100 | 80 | 100 | 0 | 90 | 0 | 0 | 0 | 30 | 0 | 40 | 30 | 30 | 0 | 0 | 0 |
| 32 | 2 | 100 | 100 | 100 | 100 | 100 | 100 | 100 | 100 | 100 | 100 | 100 | 100 | 100 | 50 | 30 | 30 |
| | 0.5 | 100 | 100 | 100 | 80 | 100 | 50 | 70 | 50 | 100 | 90 | 100 | 100 | 100 | 50 | 20 | 0 |
| | 0.125 | 100 | 100 | 100 | 0 | 50 | 0 | 20 | 0 | 80 | 30 | 100 | 100 | 90 | 50 | 20 | 0 |
| 33 | 2 | 100 | 100 | 100 | 90 | 100 | 50 | 50 | 30 | 100 | 100 | 100 | 100 | 100 | 100 | 20 | 0 |
| | 0.5 | 95 | 98 | 100 | 30 | 100 | 0 | 0 | 0 | 70 | 40 | 100 | 70 | 98 | 80 | 20 | 0 |
| | 0.125 | 50 | 30 | 100 | 0 | 90 | 0 | 0 | 0 | 30 | 20 | 100 | 50 | 98 | 0 | 0 | 0 |
| 34 | 2 | 100 | 98 | 100 | 100 | 100 | 0 | 20 | 0 | 80 | 40 | 100 | 100 | 70 | 50 | 0 | 30 |
| | 0.5 | 90 | 80 | 90 | 0 | 98 | 0 | 0 | 0 | 30 | 30 | 70 | 80 | 30 | 0 | 0 | 0 |
| | 0.125 | 80 | 70 | 90 | 0 | 98 | 0 | 0 | 0 | 20 | 0 | 60 | 80 | 30 | 0 | 0 | 0 |
| 35 | 2 | 100 | 100 | 100 | 80 | 100 | 0 | 100 | 100 | 100 | 100 | 100 | 100 | 100 | 0 | 30 | 30 |
| | 0.5 | 100 | 100 | 100 | 80 | 100 | 0 | 80 | 50 | 100 | 100 | 100 | 80 | 98 | 0 | 20 | 0 |
| | 0.125 | 100 | 100 | 100 | 30 | 100 | 0 | 30 | 0 | 80 | 40 | 30 | 30 | 60 | 0 | 0 | 0 |
| 37 | 2 | 100 | 100 | 100 | 100 | 100 | 0 | 80 | 100 | 100 | 95 | 100 | 100 | 100 | 100 | 20 | 50 |
| | 0.5 | 100 | 100 | 100 | 50 | 100 | 0 | 30 | 0 | 100 | 80 | 100 | 100 | 100 | 100 | 0 | 0 |
| | 0.125 | 95 | 80 | 100 | 0 | 98 | 0 | 0 | 0 | 70 | 20 | 90 | 90 | 90 | 50 | 0 | 0 |
| 38 | 2 | 100 | 100 | 100 | 80 | 98 | 0 | 80 | 0 | 100 | 70 | 100 | 80 | 100 | 100 | 20 | 50 |
| | 0.5 | 100 | 80 | 100 | 0 | 50 | 0 | 0 | 0 | 40 | 20 | 90 | 30 | 50 | 50 | 0 | 0 |
| | 0.125 | 40 | 30 | 98 | 0 | 0 | 0 | 0 | 0 | 20 | 0 | 30 | 30 | 20 | 30 | 0 | 0 |
| 41 | 2 | 100 | 100 | 100 | 100 | 100 | 100 | 50 | 0 | 100 | 90 | 100 | 100 | 100 | 80 | 0 | 0 |
| | 0.5 | 98 | 95 | 100 | 20 | 95 | 0 | 40 | 0 | 50 | 40 | 100 | 100 | 100 | 70 | 0 | 0 |
| | 0.125 | 50 | 30 | 100 | 0 | 95 | 0 | 0 | 0 | 20 | 20 | 80 | 100 | 80 | 0 | 0 | 0 |
| 42 | 100 | 100 | 100 | 100 | 100 | 0 | 30 | 0 | 100 | 100 | 100 | 100 | 100 | 100 | 20 | 0 | |
| | 0.5 | 100 | 100 | 100 | 50 | 100 | 0 | 0 | 0 | 98 | 100 | 100 | 100 | 100 | 70 | 0 | 0 |
| | 0.125 | 90 | 95 | 100 | 0 | 95 | 0 | 0 | 0 | 95 | 80 | 100 | 100 | 95 | 50 | 0 | 0 |
| 43 | 2 | 100 | 100 | 100 | 80 | 100 | 30 | 0 | 0 | 50 | 20 | 100 | 80 | 90 | 100 | 0 | 0 |
| | 0.5 | 95 | 60 | 100 | 0 | 100 | 0 | 0 | 0 | 20 | 0 | 95 | 100 | 40 | 50 | 0 | 0 |
| | 0.125 | 60 | 20 | 80 | 0 | 98 | 0 | 0 | 0 | 0 | 0 | 20 | 50 | 20 | 0 | 0 | 0 |
| 44 | 2 | 100 | 70 | 100 | 0 | 80 | 80 | 0 | 0 | 100 | 50 | 100 | 100 | 100 | 100 | 0 | 30 |
| | 0.5 | 70 | 0 | 00 | 0 | 30 | 80 | 0 | 0 | 80 | 50 | 80 | 100 | 80 | 0 | 0 | 0 |
| | 0.125 | 20 | 0 | 30 | 0 | 0 | 0 | 0 | 0 | 20 | 20 | 30 | 80 | 30 | 0 | 0 | 0 |
| 45 | 2 | 100 | 100 | 100 | 90 | 100 | 50 | 50 | 0 | 100 | 70 | 100 | 100 | 100 | 100 | 20 | 70 |
| | 0.5 | 100 | 80 | 100 | 20 | 70 | 0 | 0 | 0 | 80 | 20 | 100 | 80 | 90 | 0 | 0 | 0 |
| | 0.125 | 70 | 30 | 100 | 0 | 50 | 0 | 0 | 0 | 20 | 0 | 100 | 80 | 80 | 0 | 0 | 0 |
| 46 | 2 | 90 | 98 | 100 | 0 | 50 | 0 | 0 | 0 | 90 | 80 | 100 | 100 | 100 | 100 | 30 | 30 |
| | 0.5 | 50 | 0 | 80 | 0 | 30 | 0 | 0 | 0 | 80 | 30 | 100 | 100 | 98 | 100 | 20 | 0 |
| | 0.125 | 30 | 0 | 0 | 0 | 0 | 0 | 0 | 0 | 30 | 0 | 98 | 80 | 90 | 70 | 0 | 0 |
| 47 | 2 | 95 | 90 | 100 | 50 | 98 | 0 | 0 | 0 | 98 | 50 | 100 | 100 | 100 | 50 | 20 | 50 |
| | 0.5 | 95 | 20 | 98 | 0 | 50 | 0 | 0 | 0 | 50 | 20 | 100 | 80 | 90 | 0 | 0 | 0 |
| | 0.125 | 20 | 0 | 80 | 0 | 0 | 0 | 0 | 0 | 20 | 20 | 100 | 80 | 60 | 0 | 0 | 0 |
| 49 | 2 | 100 | 100 | 100 | 100 | 100 | 80 | 100 | 0 | 100 | 100 | 100 | 100 | 30 | 30 | 80 | 0 |
| | 0.5 | 100 | 100 | 100 | 0 | 100 | 0 | 90 | 0 | 100 | 100 | 80 | 0 | 30 | 0 | 30 | 0 |
| | 0.125 | 100 | 100 | 100 | 0 | 100 | 0 | 0 | 0 | 80 | 30 | 20 | 0 | 20 | 0 | 0 | 0 |

We claim:

1. A compound of the formula:

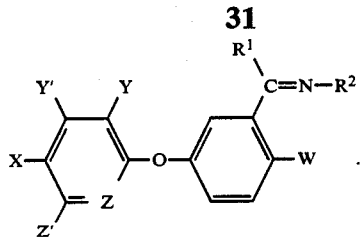

wherein:

Z is selected from the group consisting of nitrogen and —C(X')=;

W, Y, Y', X, Z' and X' are each independently selected from the group consisting of hydrogen, halogen, $NO_2$, CN, $C_1$–$C_4$ polyhalogenoalkyl, $C_1$–$C_4$ alkyl and $C_1$–$C_4$ alkoxy;

$R^1$ is selected from the group consisting of halogen, $X^2R^3$ and $NR^4R^5$;

$R^2$ is selected from the group consisting of hydrogen, halogen, allyl, propargyl, CN, $NR^4R^5$, $C(X^2)R^7$, $C(X^2)X^3R^8$, $C(X^2)NR^4R^5$, $SO_2F$, $SO_2OR^8$, $SO_2NR^4R^5$, $P(X^2)R^9R^{10}$ and $C_1$–$C_4$ alkyl substituted by one or more of each of halogen, $C_1$–$C_4$ alkoxy, $C_1$–$C_4$ alkylthio, $NO_2$, CN, phenyl, phenyl substituted by one or more halogen atoms, and a carboxyl group or one of its derivatives of the salt, ester or amide type;

$R^3$ is selected from the group consisting of $C_1$–$C_4$ alkyl, substituted $C_1$–$C_4$ alkyl, allyl and propargyl;

$R^4$ is selected from the group consisting of hydrogen, $C_1$–$C_4$ alkyl, substituted $C_1$–$C_4$ alkyl, $C_3$–$C_7$ cycloalkyl, substituted $C_3$–$C_7$ cycloalkyl, phenyl, substituted phenyl, allyl, propargyl, $C_1$–$C_4$ alkylcarbonyl and $C_1$–$C_4$ alkylsulphonyl;

$R^5$ is selected from the group consisting of hydrogen, $C_1$–$C_4$ alkyl, substituted $C_1$–$C_4$ alkyl, $C_3$–$C_7$ cycloalkyl, substituted $C_3$–$C_7$ cycloalkyl, phenyl, substituted phenyl, allyl, propargyl, $C_1$–$C_4$ alkylcarbonyl, $C_1$–$C_4$ alkylsulphonyl, a cation and $OR^6$, wherein $R^6$ is selected from the group consisting of hydrogen, a cation, $C_1$–$C_4$ alkyl and substituted $C_1$–$C_4$ alkyl;

$X^2$ and $X^3$ are each independently selected from the group consisting of oxygen and sulphur;

$R^7$ is selected from the group consisting of hydrogen, $C_1$–$C_{12}$ alkyl, substituted $C_1$–$C_{12}$ alkyl, $C_3$–$C_7$ cycloalkyl, substituted $C_3$–$C_7$ cycloalkyl, phenyl, substituted phenyl, $C_2$–$C_4$ alkenyl and $C_2$–$C_4$ alkynyl;

$R^8$ is selected from the group consisting of hydrogen, $C_1$–$C_4$ alkyl, substituted $C_1$–$C_4$ alkyl, $C_3$–$C_7$ cycloalkyl, substituted $C_3$–$C_7$ cycloalkyl, phenyl, substituted phenyl, $C_2$–$C_4$ alkenyl, $C_2$–$C_4$ alkynyl and a cation;

$R^9$ and $R^{10}$ are each independently selected from the group consisting of hydrogen, $C_1$–$C_4$ alkyl, substituted $C_1$–$C_4$ alkyl, hydroxyl, OM, wherein M is a cation, halogen, $X^2R^3$ and $NR^4R^5$, wherein $R^3$, $R^4$, $R^5$ and $X^2$ are as previously defined above, provided that (a) $R^2$ is not $COOCH_3$ when $R^1$ is $OCH_3$, W is $NO_2$, Y' and Z' are H, X is $CF_3$, Y is Cl and Z is —CH=, and provided futher that (b) $R^2$ is not H when X is $NO_2$.

2. The compound of claim 1 wherein:

W is selected from the group consisting of hydrogen, halogen, $NO_2$ and CN;

Y is selected from the group consisting of hydrogen, halogen, $NO_2$, CN, $CF_3$ and $CH_3$;

Y', Z' and X' are each independently selected from the group consisting of hydrogen and halogen;

X is selected from the group consisting of halogen, $NO_2$, $CF_3$, $CH_3$ and $C_2H_5$;

$R^1$ is selected from the group consisting of halogen $X^2R^3$ and $NR^4R^5$;

$R^2$ is selected from the group consisting of hydrogen, halogen, allyl, propargyl, CN, $NR^4R^5$, $C(X^2)R^7$, $C(X^2)X^3R^8$, $C(X^2)NR^4R^5$, $SO_2F$, $SO_2OR^8$, $SO_2NR^4R^5$, $P(X^2)R^9R^{10}$ and alkyl substituted by
 one or more halogen,
 one or more alkoxy or alkylthio,
 one or more $NO_2$ or CN,
 phenyl optionally substituted by one or more halogen, or
 carboxyl;

$R^3$ is selected from the group consisting of allyl, propargyl and alkyl, the alkyl group being optionaly substituted by:
 one or more halogen
 one or more alkoxy or alkylthio
 one or more $NO_2$ or CN,
 a phenyl group, itself optionally substituted by one or more halogen atoms,
 a carboxyl group or one of its derivatives of the salt, ester or amide type or
 an alkylcarbonyl group;

$R^4$ is selected from the group consisting of hydrogen, allyl, propargyl, alkylcarbonyl, alkylsulphonyl, a phenyl group optionally substituted by one or more halogen atoms, alkyl and cycloalkyl, the last two being optionally substituted by
 one or more halogen, alkoxy or alkylthio groups;

$R^5$ has one of the meanings given for $R^4$ or represents an alkali metal cation or ammonium cation or a group $OR^6$, $R^6$ being hydrogen, an alkali metal cation or ammonium cation, or an alkyl group optionally substituted by carboxyl group or one of its derivates of the salt, ester or amide type;

$R^4$ and $R^5$ can optionaly together form a single divalent alkylene radical;

$X^2$ and $X^3$ are each oxygen or sulphur;

$R^7$ is selected from the group consisting of alkenyl, alkynyl, hydrogen, alkyl and cycloalkyl, the last two being optionally substituted by
 one or more halogen atoms,
 one or more alkoxy or alkylthio groups having from 1 to 4 carbon atoms,
 a phenyl group optionally substituted by one or more halogen atoms,
 a carboxyl group or one of its derivatives of the salt, ester or amide type, or
 a phenyl group optionally substituted by one or more halogen atoms, nitro groups or alkyl radicals;

$R^8$ is a metal cation or ammonium cation or has one of the meanings given for $R^7$; and $R^9$ and $R^{10}$ are independently or simultaneously $R^1$, hydrogen, an alkyl group optionally substituted by one or more halogen atoms, a hydroxyl group or a group OM, wherein M is a metal cation or ammonium cation.

3. The compound of claim 2 wherein Z is N or —C(X'); W is $NO_2$ or Cl; Y is Cl; Y' and Z' are H; X is Cl or $CF_3$; and X' is Cl, F or H.

4. The compound of claim 3 wherein $R^1$ is an alkoxy or thioalkoxy group having from 1 to 4 carbon atoms.

5. The compound of claim 4 wherein,
$R^2$ is hydrogen, $C_1$-$C_4$ alkyl, substituted $C_1$-$C_4$ alkyl, allyl, $C(O)R^7$, $C(O)OR^8$ or

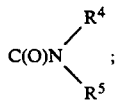
;

$R^3$ and $R^8$ are $C_1$-$C_4$ alkyl;
$R^4$, $R^5$ and $R^6$ are independently or simultaneously hydrogen or $C_1$-$C_4$ alkyl;
$R^7$ is $C_1$-$C_4$ alkyl or alkenyl; and
$R^9$ and $R^{10}$ are independently or simultaneously $C_1$-$C_4$ alkyl or alkoxy.

6. The compound of claim 3 wherein $R^1$ is Cl.

7. The compound of claim 3 wherein $R^2$ is Cl or F.

8. The compound of claim 3 wherein $R^2$ is $C_1$-$C_4$ alkyl substituted by one or more halogen atoms, alkoxy or alkylthio groups having from 1 to 4 carbon atoms, $NO_2$, CN, phenyl, substituted phenyl, a carboxyl group or the salt, ester or amide derivative thereof.

9. The compound of claim 3 wherein $R^2$ is $COOR^8$ and $R^8$ is selected from the group consisting of a cation, hydrogen, $C_1$-$C_4$ alkyl, substituted $C_1$-$C_4$ alkyl, $C_3$-$C_7$ cycloalkyl, substituted $C_3$-$C_7$ cycloalkyl, phenyl, substituted phenyl, $C_1$-$C_4$ alkenyl, and $C_1$-$C_4$ alkynyl.

10. The compound of claim 3 wherein $R^3$ is $C_1$-$C_4$ alkyl substituted by one or more halogen, alkoxy or alkylthio groups having from 1 to 4 carbon atoms, $NO_2$, CN, phenyl, substituted phenyl, $C_1$-$C_4$ alkylcarbonyl and a $C_1$-$C_4$ carboxyl group or the salt, ester or amide derivative thereof.

11. The compound of claim 10 wherein said alkyl is substituted by $COOR^8$ and $R^8$ is selected from the group consisting of a cation, hydrogen $C_1$-$C_4$ alkyl, substituted $C_1$-$C_4$ alkyl, $C_3$-$C_7$ cycloalkyl, substituted $C_3$-$C_7$ cycloalkyl, phenyl, substituted phenyl, $C_1$-$C_4$ alkenyl and $C_1$-$C_4$ alkynyl.

12. The compound of claim 3 wherein $R^4$ is alkyl or cycloalkyl which are substituted by one or more halogen, alkoxy or alkylthio groups having from 1 to 4 carbon atoms.

13. The compound of claim 3 wherein $R^4$ is phenyl substituted by one or more halogen atoms.

14. The compound of claim 3 wherein $R^4$ is methanesulphonyl.

15. The compound of claim 3 wherein $R^5$ is an alkali metal cation or ammonium cation.

16. The compound of claim 3 wherein $R^5$ is $OR^6$ and $R^6$ is an alkali metal cation or an ammonium cation.

17. The compound of claim 3 wherein $R^7$ is $C_1$-$C_{12}$ alkyl or $C_3$-$C_7$ cycloalkyl which are substituted by one or more halogen, alkoxy or alkylthio group having from 1-4 carbon atoms, phenyl, substituted phenyl, a $C_1$-$C_4$ carboxyl group or the salt, ester or amide derivative thereof.

18. The compound of claim 3 wherein $R^7$ is alkenyl or alkynyl having from 2 to 4 carbon atoms.

19. The compound of claim 3 wherein $R^8$ is a metal cation or ammonium cation.

20. The compound of claim 3 wherein $R^9$ and $R^{10}$ are independently selected from the group OM and M is a metal cation or ammonium cation.

21. The compound of claim 3 wherein $R^1$ is $NR^4R^5$ and $R^4$ is H.

22. The compound of claim 1 having the formula

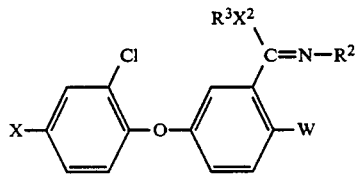

wherein X, $R^2$, $R^3X^2$, and W are as defined in claim 1.

23. The compound of claim 22 wherein X is $CF_3$; W is $NO_2$; $X^2R^3$ is $OCH_3$;
and $R^2$ is selected from the group consisting of H, $CH_2CH_2Cl$, $CH_2CH=CH_2$, $SO_2F$, $SO_2OC_2H_5$, $COCH_3$, $COC_2H_5$, $CO(CH_2)_2CH_3$, $COCH(CH_3)_2$, $COCHCl_2$, $COCCl_3$, $CONHC_2H_5$, $SO_2NHCH_3$, $SO_2NH_2$,

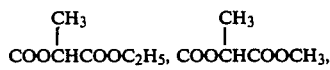

$COOC_2H_5$, $CONH_2$, $CONHCH_3$, $CONH(CH_2)_2CH_3$, $CONHCH(CH_3)_2$,

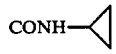
, $CONHCH_2CH=CH_2$, $CONHCH_2C\equiv CH$, $CONH(CH_2)_3CH_3$, $CON(CH_3)_2$,

and $CON(C_2H_5)_2$.

24. The compound of claim 22 wherein X is Cl, W is $NO_2$, $X^2R^3$ is $OC_2H_5$, and $R_2$ is H or $CONH_2H$.

25. The compound of claim 22 wherein X is $CF_3$, W is $NO_2$, $X^2R^3$ is $OC_2H_5$ and $R_2$ is H, $CONHC_2H_5$ or $CONHCH_3$.

26. The compound of claim 22 wherein X is $CF_3$, W is Cl, $X^2R^3$ is $OCH_3$ and $R_2$ is H.

27. The compound of claim 22 wherein X is Cl, W is $NO_2$, $X^2R^3$ is $OCH_3$ and $R^2$ is $CONHCH_3$ or $CONHC_2H_5$.

28. The compound of claim 22 wherein X is $CF_3$, W is $NO_2$, $X^2R^3$ is $SCH_3$ and $R_2$ is selected from the group consisting of $CONHCH_3$, $CONHC_2H_5$, $CONH_2$, $CONHCH_2CH=CH_2$, $CON(CH_3)_2$,

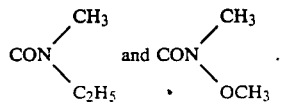

29. The compound of claim 22 having the formula:

30. The compound of claim 22 having the formula:

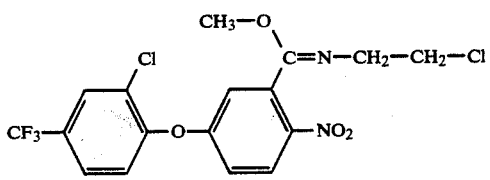

31. The compound of claim 22 having the formula:

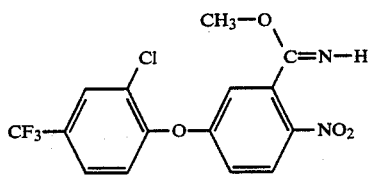

32. The compound of claim 1 having the formula:

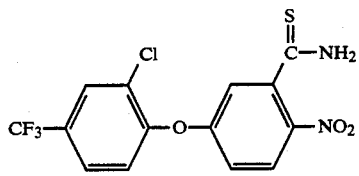

33. The compound of claim 1 having the formula:

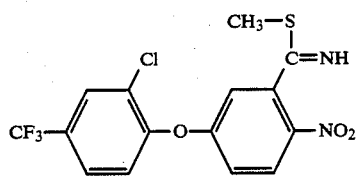

34. A compound having the formula:

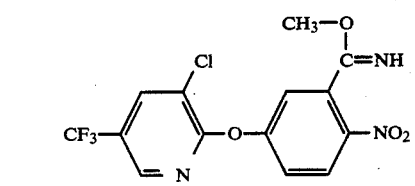

35. A herbidical composition comprising as the active ingredient a compound of formula I as defined in claim 1 and at least one inert carrier that is agriculturally acceptable.

36. The herbicidal composition of claim 35, which comprises from about 0.5 to about 95% of the active ingredient.

37. The herbicidal composition of claim 36, which comprises from about 1 to about 95% of carrier and from about 0.1 to about 20% of a surface-active agent.

38. A compound of the formula:

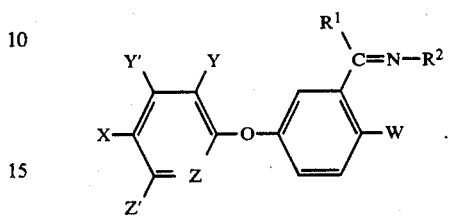

wherein:
Z is N or —C(X');
W is $NO_2$ or Cl;
Y is Cl;
Y' and Z' are H;
X is Cl or $CF_3$; and
X' is Cl, F or H;
$R^1$ is selected from the group consisting of halogen, $X^2R^3$ and $NR^4R^5$;
$R^2$ is $C(X^2)NR^4R^5$ or $C(X^2)X^3R^8$;
$R^3$ is selected from the group consisting of allyl, propargyl and $C_1$-$C_4$ alkyl
  one or more halogen,
  one or more alkoxy or alkylthio,
  one or more $NO_2$ or CN,
  a phenyl group, itself optionally substituted by one or more halogen atoms,
  a carboxyl group or one of its derivatives of the salt, ester or amide type, or,
  an alkylcarbonyl group;
$R^4$ is selected from the group consisting of hydrogen, $C_1$-$C_4$ alkyl, $C_3$-$C_7$ cycloalkyl, a phenyl group optionally substituted by one or more halogen atoms, allyl, propargyl, $C_1$-$C_4$ alkylcarbonyl and $C_1$-$C_4$ alkylsulphonyl, the alkyl and cycloalkyl being optionally substituted by one or more halogen, alkoxy or alkylthio groups;
$R^5$ is selected from the group consisting of $R^4$, an alkali metal or ammonium cation or a group $OR^6$, $R^6$ being hydrogen, an alkali metal cation or ammonium cation, $C_1$-$C_4$ alkyl optionally substituted by a carboxyl group or one of its derivatives of the salt, ester or amide type;
$X^2$ and $X^3$ are each independently oxygen or sulphur;
$R^7$ is selected from the group consisting of hydrogen, $C_1$-$C_{12}$ alkyl, $C_3$-$C_7$ cycloalkyl, $C_2$-$C_4$ alkenyl, $C_2$-$C_4$ alkynyl, wherein the alkyl and cycloalkyl are optionally substituted by
  one or more halogen atoms,
  one or more alkoxy or alkylthio groups having from 1 to 4 carbon atoms,
  a phenyl group optionally substituted by one or more halogen atoms,
  a carboxyl group or one of its derivatives of the salt, ester or amide type, or
  a phenyl group optionally substituted by one or more halogen atoms, nitro groups or alkyl radicals.

* * * * *